(12) United States Patent
Tang et al.

(10) Patent No.: US 10,561,084 B2
(45) Date of Patent: Feb. 18, 2020

(54) **MOLECULAR MARKERS FOR BLACKLEG RESISTANCE GENE RLM2 IN *BRASSICA NAPUS* AND METHODS OF USING THE SAME**

(71) Applicant: Dow AgroSciences LLC, Indianapolis, IN (US)

(72) Inventors: Shunxue Tang, Carmel, IN (US); Jianwei Zhao, Saskatoon (CA)

(73) Assignee: Dow AgroScience LLC, Indianapolis, IN (US)

( * ) Notice: Subject to any disclaimer, the term of this patent is extended or adjusted under 35 U.S.C. 154(b) by 1113 days.

(21) Appl. No.: 14/479,907

(22) Filed: Sep. 8, 2014

(65) Prior Publication Data

US 2015/0074850 A1  Mar. 12, 2015

Related U.S. Application Data

(60) Provisional application No. 61/875,831, filed on Sep. 10, 2013.

(51) Int. Cl.
*A01H 1/04* (2006.01)
*C12Q 1/6895* (2018.01)

(52) U.S. Cl.
CPC ............. *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2013/0269065 A1* 10/2013 Li ........................ C07K 14/415
800/301

OTHER PUBLICATIONS

Long et al. (Theor. Appl. Genet. (2011) 122: pp. 1223-1231).*
Gen Bank Accession #AGC13588 (2013, https://www.ncbi.nlm.nih.gov/protein/440574322).*
Gen Bank Accession #JX880110 (2013, https://www.ncbi.nlm.nih.gov/nuccore/JX880110).*
Larkan et al (2015, Plant Biotechnol. J. 13:983-992), including supplement.*

* cited by examiner

*Primary Examiner* — Anne Kubelik

(57) ABSTRACT

This disclosure concerns methods and compositions for identifying canola plants that have a blackleg resistant phenotype. Some embodiments concern molecular markers to identify, select, and/or construct blackleg resistant plants and germplasm, or to identify and counter-select plants that are susceptible or have low resistance to blackleg disease. Some embodiments concern molecular markers to identify, select, and/or construct blackleg resistant plants that carry the rlm2 gene. This disclosure also concerns canola plants comprising a blackleg resistant phenotype that are generated by methods utilizing at least one marker described herein.

1 Claim, 2 Drawing Sheets

Specification includes a Sequence Listing.

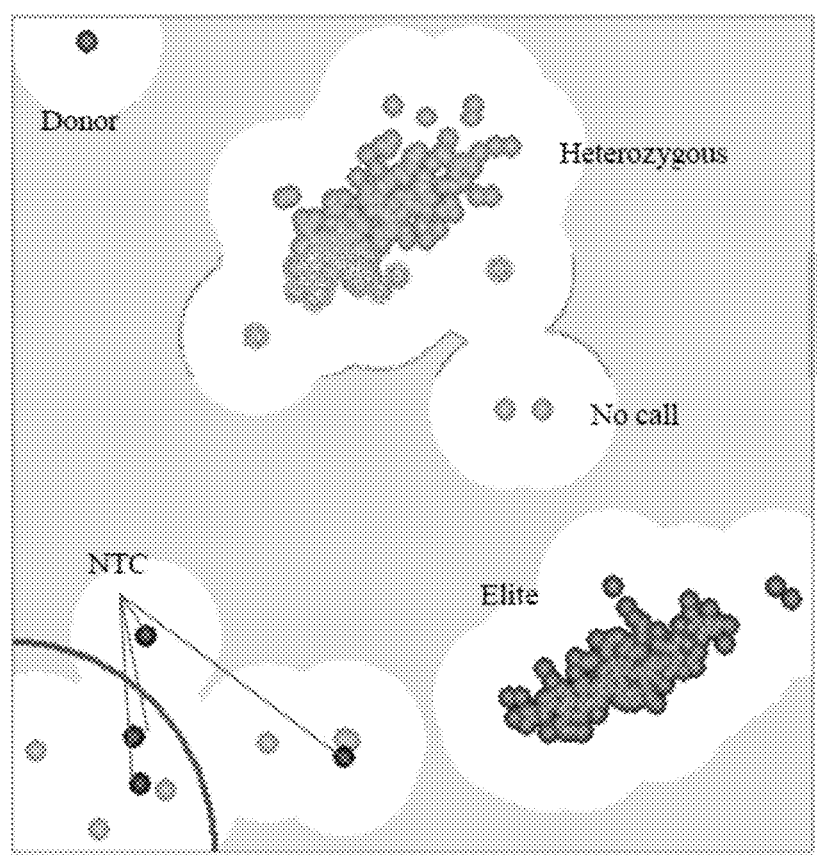
Figure 1. Example of a distribution graph for a BC1F1 population based on Relative Fluorescence Units (RFU).

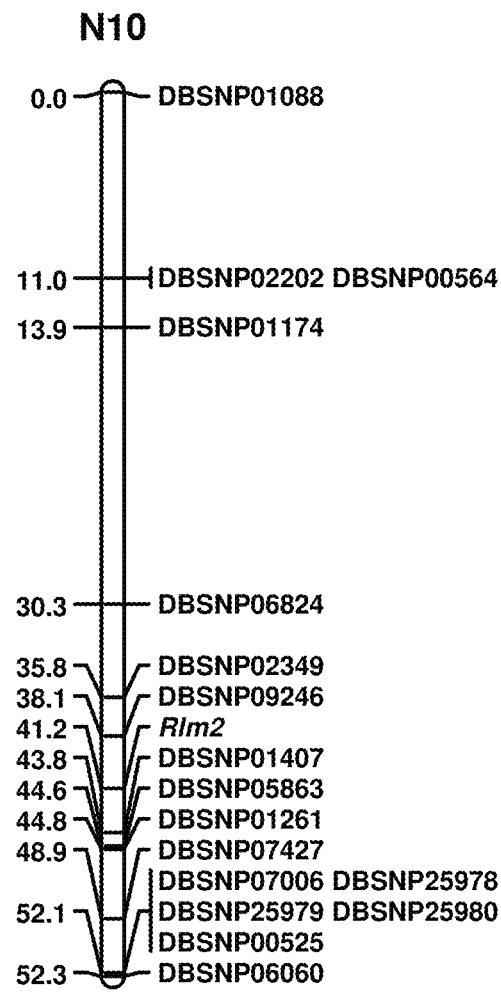
Figure 2. Canola linkage group N10; the four closest SNP markers flank Rlm2.

MOLECULAR MARKERS FOR BLACKLEG RESISTANCE GENE RLM2 IN *BRASSICA NAPUS* AND METHODS OF USING THE SAME

CROSS REFERENCE TO RELATED APPLICATIONS

This application claims priority from and benefit of, U.S. Provisional Application 61/875,831, filed 10 Sep. 2013. The entire contents of this application are hereby incorporated by reference into this application.

FIELD OF THE DISCLOSURE

The present disclosure relates to compositions and methods for identifying canola plants that have resistance to blackleg disease, where the methods use molecular genetic markers to identify, select and/or construct blackleg resistant plants, and specifically to select or construct plants with the blackleg resistance gene Rlm2. The disclosure also relates to canola plants that are blackleg resistant that are generated by the methods of the invention.

BACKGROUND

Blackleg is a serious disease of canola that can result in significant yield loss in susceptible varieties in Canada, Europe, and Australia. Blackleg is the most common name, but stem canker or *Phoma* stem canker are also used for this disease. It is caused by the fungus *Leptosphaeria maculans*. In Saskatchewan a highly aggressive strain of the blackleg fungus was first detected in 1975, but now occurred in most canola-growing areas in western Canada.

Canola disease field surveys are conducted annually in the main canola production regions of western Canada. Disease surveys from recent years indicate that blackleg is commonly found in 35 to 55 percent of crops surveyed. Average disease incidence values (percentage of plants showing blackleg symptoms) are typically one percent for basal stem cankers and three percent for lesions occurring elsewhere on the stem. Lesions occurring elsewhere on the stem will have less impact on seed yield and quality than will basal stem cankers. The highest incidence values are often observed in crops that had received hail damage.

As is indicated in the disease surveys, it is not unusual to observe blackleg symptoms in canola crops, even when resistant varieties are being grown. However, to prevent blackleg from negatively impacting seed yield and quality, it is important to be familiar with blackleg symptoms, the disease cycle, and disease management practices.

Blackleg is the most serious disease of canola in Australia. The severity of blackleg has risen in recent years due to increased acreage and intensity of production. Although not common, yield losses of 50 percent and greater have been recorded in some seasons with up to 90 percent yield loss occurring in cases where *L. maculans* has overcome major blackleg resistance genes within certain varieties.

In the autumn and winter, rainfall triggers spore release from the stubble. Within two weeks of spores landing on canola cotyledons and young leaves, clearly visible off-white coloured lesions develop, within the lesion pycnidial fruiting bodies (dark coloured dots) release rain-splashed spores. Blackleg infections may occur on cotyledons, leaves, stems and pods. The plant is susceptible to blackleg infection from the seedling to pod-set stages. Lesions occurring on the leaves are dirty white and are round to irregularly. On stems, blackleg lesions can be quite variable, but are usually found at the base of the stem, or at points of leaf attachment. Once a lesion has formed, the fungus grows within the plants vascular system to the crown where it causes the crown of the plant to rot, resulting in a canker. Severe canker will sever the roots from the stem, whereas a less severe infection will result in internal infection of the crown restricting water and nutrient flow within the plant. Stem lesions may be up to several inches in length, and are usually white or grey with a dark border. Stem lesions may also appear as a general blackening at the base. Severe infection usually results in a dry rot or canker at the base of the stem. The stem becomes girdled and, as plants ripen prematurely, the crop is more likely to lodge. Seed may be shriveled and pods shatter easily at harvest, resulting in seed loss.

In recent years blackleg symptoms have also been found in the plant roots, this root infection in severe cases appears to cause the entire plant to die prematurely. The root rot form of the disease is caused by the same blackleg strains that cause the stem canker and management practices to control normal blackleg are the same for the root rot form of the disease.

With increasing acres of canola and often tighter rotations, blackleg disease has again started to become an important yield and quality reducing disease.

Varietal resistance is the best defense, to date, against blackleg disease. The development of blackleg resistant varieties has lead to reduced economic losses due to blackleg. As a result, many farmers are growing resistant varieties and they have been able to get away with tighter and tighter rotations. Preliminary observations from the 2010 canola disease survey show that in Manitoba the R-rated varieties are starting to show higher incidence and severity of the blackleg disease. *L. maculans* has developed new variants and these new variants are now able to infect the earlier R-rated canola varieties.

When the blackleg resistant varieties were first developed, researchers categorized the pathogen into "PG" pathogroups, which were based on the infectivity of an isolate on 3 varieties—Westar, Glacier and Quinta. With changing blackleg populations, the PG classification is insufficient to describe newer variants. This means the PG system cannot identify variability among isolates as a result of sources of resistance not found in 'Quinta' and 'Glacier'. Based on molecular markers, pathogen isolates have been able to be classified into PG groups, much quicker than the traditional plant inoculation method (Dusabenyagasani, M., and Fernando, W. G. D. 2008).

In a newer approach, by using varieties or lines of *Brassica* spp. carrying 14 specific resistance genes, new isolates of *L. maculans* can be differentiated or characterized into races based on the reactions observed. Rimmer (2007) had reported these 14 genes of specific resistance, designated Rlm 1 to Rlm 10 and LepR1 to LepR4. A study of 96 western Canadian isolates of blackleg fungus, using ten resistance genes indicated considerable variation in the pathogen population for many of these genes (Kutcher et al. 2010).

There are numerous steps in the development of any novel, desirable plant germplasm. Plant breeding programs combine desirable traits from two or more cultivars or various broad-based sources into breeding pools, from which cultivars are developed by selfing and selection of desired phenotypes. The new cultivars are evaluated to determine which have commercial potential. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Backcross breeding is used to transfer favorable alleles of one or a few genes for a highly heritable trait into a desirable cultivar. This approach has been used extensively for breeding disease-resistant cultivars. Various recurrent selection techniques are used to improve quantitatively-inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year (based on comparisons to an appropriate standard), overall value of the advanced breeding lines, and the number of successful cultivars produced per unit of input (e.g., per year, per dollar expended, etc.). Promising advanced breeding lines are then thoroughly tested and compared to appropriate standards in environments representative of the commercial target area(s) for three or more years. Candidates for new commercial cultivars are selected from among the best lines; those still deficient in a few traits may be used as parents to produce new populations for further selection. These processes, which lead to the final step of marketing and distribution, usually take from 8 to 12 years from the time the first cross is made. Therefore, development of new cultivars is a time-consuming process that requires precise forward planning, efficient use of resources, and a minimum of changes in direction.

A most difficult task in plant breeding is the identification of individuals that are genetically superior. One method of identifying a superior plant is to observe its performance relative to other experimental plants and to a widely grown standard cultivar. If a single observation is inconclusive, replicated observations provide a better estimate of its genetic worth. This task is so difficult, because (for most traits) the true genotypic value is masked by other confounding plant traits or environmental factors.

The goal of canola plant breeding is to develop new, unique, and superior canola cultivars and hybrids. The breeder initially selects and crosses two or more parental lines, followed by repeated selfing and selection, producing many new genetic combinations. The breeder can theoretically generate billions of different genetic combinations via crossing, selfing, and mutagenesis. Such a breeder has no direct control of the process at the cellular level. Therefore, two breeders will never develop the same line, or even very similar lines, having the same canola traits.

Each year, the plant breeder selects the germplasm to advance to the next generation. This germplasm is grown under unique and different geographical, climatic, and soil conditions. Further selections are then made, during and at the end of the growing season. The cultivars that are developed are unpredictable. This unpredictability is due to the breeder's selection, which occurs in unique environments, and which allows no control at the DNA level (using conventional breeding procedures), with millions of different possible genetic combinations being generated. A breeder of ordinary skill in the art cannot predict the final resulting lines he develops, except possibly in a very gross and general fashion. Similarly, the same breeder cannot produce the same cultivar twice by using the exact same original parents and the same selection techniques. This unpredictability results in the expenditure of large amounts of resources, monetary and otherwise, to develop superior new canola cultivars.

The development of new canola cultivars requires the development and selection of canola varieties, crossing of these varieties, and selection of superior hybrid crosses. Hybrid seed is produced by manual crosses between selected male-fertile parents, or by using male sterility systems. These hybrids are selected for certain single gene traits (e.g., pod color, flower color, pubescence color, and herbicide resistance) that indicate that the seed is truly a hybrid. Data on parental lines, as well as the phenotype of the hybrid, influence the breeder's decision regarding whether to continue with the specific hybrid cross.

Pedigree breeding is used commonly for the improvement of self-pollinating crops. In pedigree breeding, two parents that possess favorable, complementary traits are crossed to produce $F_1$ progeny. An $F_2$ population is produced by selfing one or several plants from the $F_1$ progeny generation. Selection of the best individuals may begin in the $F_2$ population; then, beginning in the $F_3$, the best individuals in the best families are selected. To improve the effectiveness of selection for traits with low heritability, replicated testing of families can begin in the $F_4$ generation. At an advanced stage of inbreeding (e.g., $F_6$ or $F_7$), the best lines or mixtures of lines with similar phenotypes are tested for potential release as new cultivars. Mass and recurrent selections can be used to improve populations of either self- or cross-pollinating crops. A genetically variable population of heterozygous individuals may be either identified or created by intercrossing several different parents. The best plants may be selected based on individual superiority, outstanding progeny, or excellent combining ability. The selected plants are intercrossed to produce a new population, in which further cycles of selection may be continued.

Backcross breeding has been used to transfer genes for a simply- and highly-heritable trait into a desirable homozygous cultivar, or inbred line, which is the recurrent parent. The source of the trait to be transferred is the "donor parent." The resulting plant is expected to have the attributes of the recurrent parent (e.g., cultivar), and the desirable trait transferred from the donor parent. After the initial cross, individuals possessing the phenotype of the donor parent are selected, and repeatedly crossed (backcrossed) to the recurrent parent. The resulting plant is expected to have the attributes of the recurrent parent and the desirable trait transferred from the donor parent.

In canola breeding, the "single-seed descent procedure" refers to the planting of a segregating population, followed by harvesting a sample of one seed per resulting plant, and using the harvested one-seed sample to plant the next generation. When the population has been advanced from the $F_2$ generation to the desired level of inbreeding, the plants from which lines are derived will each trace to different $F_2$ individuals. The number of plants in a population declines each generation, due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest seeds from each plant in a population and thresh them together to form a bulk. Part of the bulk is used to plant the next generation, and part is put in reserve. This procedure has been referred to as modified single-seed descent. The multiple-seed procedure has been used to save labor involved in the harvest. It is considerably faster to remove seeds with a machine, than to remove one seed from each by hand for the single-seed procedure. The multiple-seed procedure also makes it possible to plant the same number of seeds of a population for each generation of inbreeding. Enough seeds are harvested to compensate for the number of plants that did not germinate or produce seed.

Proper testing should detect any major faults and establish the level of superiority or improvement of a new cultivar over current cultivars. In addition to showing superior performance, there should be a demand for a new cultivar that is compatible with industry standards, or that creates a new market. The testing preceding release of a new cultivar should take into consideration research and development costs as well as technical superiority of the final cultivar. The introduction of a new cultivar can incur additional costs to the seed producer, the grower, the processor, and the consumer due to special required advertising and marketing, altered seed and commercial production practices, and new product utilization. For seed-propagated cultivars, it must be feasible to produce seed easily and economically.

It is the goal of the plant breeder to select plants and enrich the plant population for individuals that have desired traits, for example, disease resistance or blackleg resistance, leading ultimately to increased agricultural productivity. Consistent with the foregoing, a continuing goal of canola breeders is to develop stable, high-yielding cultivars that are agronomically sound. Current goals include maximization of the amount of grain produced on the land used, and the supply of food for both animals and humans. To accomplish these goals, the canola breeder must select and develop canola plants that have traits that result in superior cultivars, and do so in the most cost-effective manner. Molecular markers may be used in the process of marker-assisted selection (MAS) to aid in the identification and selection of individuals or families of individuals that possess inherited attributes that are linked to the markers.

BRIEF SUMMARY OF THE DISCLOSURE

Molecular markers that are linked to blackleg resistance may be used to facilitate marker-assisted selection for the blackleg resistance trait in canola. Marker-assisted selection provides significant advantages with respect to time, cost, and labor, when compared to blackleg resistance phenotyping. Disclosed herein are particular markers identified to be within or near blackleg resistance regions in the canola genome that are polymorphic in parent genotypes and linked (e.g., tightly-linked) to a blackleg resistance phenotype. These markers, offer superior utility in marker-assisted selection of canola plants and cultivars having blackleg resistance.

Described herein are methods of identifying a first canola plant that displays blackleg resistance or germplasm comprised within such a canola plant. A first canola plant or germplasm that displays blackleg resistance may in some examples be a plant or germplasm comprising blackleg resistance (or improved blackleg resistance) than is observed in a parental plant or germplasm of the first plant or germplasm. A first canola plant or germplasm that displays blackleg resistance may in some examples be a plant or germplasm comprising a better blackleg resistance than is observed in a particular conventional plant or germplasm of the same species (e.g., canola) as the first plant or germplasm. Some embodiments of such methods may comprise detecting in the first canola plant or germplasm at least one marker linked to blackleg resistance, wherein the at least one marker is selected from the group consisting of: DBSNP02349, DBSNP09246, DBSNP01407, DBSNP05863, DBSNP01261, and DBSNP07427; and markers linked (e.g., tightly-linked) to any of DBSNP02349, DBSNP09246, DBSNP01407, DBSNP05863, DBSNP01261, and DBSNP07427.

Also described are methods of producing a canola plant or germplasm having blackleg resistance. Some embodiments of such methods may comprise introgressing at least one marker linked to blackleg resistance from a first canola plant or germplasm into a second canola plant or germplasm to produce a canola plant or germplasm that is likely to have blackleg resistance. In such examples, the at least one marker may be selected from the group consisting of: DBSNP02349, DBSNP09246, DBSNP01407, DBSNP05863, DBSNP01261, and DBSNP07427. A canola plant or germplasm produced by the foregoing methods is also included in particular embodiments.

Also described are methods of producing a canola plant or germplasm having blackleg resistance. Some embodiments of such methods may comprise introgressing at least one marker linked to blackleg resistance from a first canola plant or germplasm into a second canola plant or germplasm to produce a canola plant or germplasm that is likely to have blackleg resistance. In such examples, the at least one marker may be selected from the group consisting of: DBSNP09246, DBSNP01407, DBSNP05863, and DBSNP01261. A canola plant or germplasm produced by the foregoing methods is also included in particular embodiments.

Some embodiments include methods for producing a transgenic canola plant. Examples of such methods may comprise introducing one or more exogenous nucleic acid molecule(s) into a target canola plant or progeny thereof, wherein at least one of the one or more exogenous nucleic acid molecule(s) comprises a canola genomic nucleotide sequence that is linked to at least one marker that is linked to blackleg resistance, or wherein at least one of the one or more exogenous nucleic acid molecule(s) comprises a nucleotide sequence that is specifically hybridizable to a nucleotide sequence that is linked to at least one marker that is linked to blackleg resistance. A marker that is linked to blackleg resistance may be selected from the group consisting of: DBSNP02349, DBSNP09246, DBSNP01407, DBSNP05863, DBSNP01261, and DBSNP07427 and markers linked to any of DBSNP02349, DBSNP09246, DBSNP01407, DBSNP05863, DBSNP01261, and DBSNP07427. In certain examples the foregoing methods for producing a transgenic canola plant, a resulting transgenic canola plant may comprise blackleg resistance.

Some embodiments include systems and kits for identifying a canola plant that is likely to comprise blackleg resistance. Particular examples of such systems and kits may comprise a set of nucleic acid probes, each comprising a nucleotide sequence that is specifically hybridizable to a nucleotide sequence that is linked in canola to at least one marker that is linked to blackleg resistance. A marker that is linked in canola to blackleg resistance may be selected from the group consisting of: DBSNP02349, DBSNP09246, DBSNP01407, DBSNP05863, DBSNP01261, and DBSNP07427 and markers linked to any of DBSNP02349, DBSNP09246, DBSNP01407, DBSNP05863, DBSNP01261, and DBSNP07427. Particular examples of systems and kits for identifying a canola plant that is likely to comprise blackleg resistance may also comprise a detector that is configured to detect one or more signal outputs from the set of nucleic acid probes, or an amplicon thereof, thereby identifying the presence or absence of the at least one marker that is linked to blackleg resistance. Specific examples include instructions that correlate the presence or absence of the at least one marker with the likely resistance to blackleg.

BRIEF DESCRIPTION OF THE FIGURES

FIG. 1 is an example of a distribution graph for a BC1F1 population based on Relative Fluorescence Units (RFU). Clusters for the donor, heterozygous and elite genotypes are shown. NTC represents the no template controls.

FIG. 2 shows Canola linkage group N10 constructed with 708 BC1F1 progeny of Nex845CL/NT152344//Nex845CL and genotyped with 17 SNP markers. The four closest SNP markers, DBSNP09246, DBSNP01407, DBSNP05863 and DBSNP01261, flank Rlm2.

DETAILED DESCRIPTION

Overview of Several Embodiments

It is desirable for a number of reasons to grow canola having blackleg resistance. Embodiments of the invention include, for example, compositions and methods for identifying canola plants comprising a blackleg resistance and/or germplasm carrying a genotype that is predictive and determinative of a blackleg resistant phenotype. Methods of making such canola plants and germplasm are included in some embodiments. Such methods may include, for example and without limitation, introgression of desired blackleg resistance marker alleles and/or genetic transformation methods. Canola plants and/or germplasm made by the methods such as the foregoing are included in particular embodiments. Systems and kits for selecting canola plants comprising a blackleg resistance and/or germplasm carrying a genotype that is predictive and determinative of blackleg resistance are also a feature of certain embodiments.

The identification and selection of canola plants comprising a blackleg resistance using MAS are capable of providing an effective and environmentally friendly approach for generating plants with desirable disease resistance. Embodiments of the present invention provide a number of canola marker loci and QTL chromosome intervals that demonstrate statistically significant co-segregation with (and therefore are predictive and determinative of) blackleg resistance. Detection of these markers, or additional loci linked to the markers that are therefore equivalent thereto, may be used in marker-assisted canola breeding programs to produce blackleg resistant plants and germplasm.

Some embodiments provide methods for identifying a first canola plant or germplasm (e.g., a line or variety) that displays blackleg resistance. In some examples, at least one allele of one or more marker locus (e.g., a plurality of marker loci) that is linked (e.g., tightly-linked) with a blackleg resistance trait is/are detected in the first canola plant or germplasm. The marker loci may be selected from the loci in FIG. 2 including: DBSNP02349, DBSNP09246, DBSNP01407, DBSNP05863, DBSNP01261, and DBSNP07427, and other markers that are linked to at least one of the foregoing QTL markers.

In some examples, a plurality of maker loci may be selected or identified in the same plant or germplasm. All combinations of, for example, DBSNP02349, DBSNP09246, DBSNP01407, DBSNP05863, DBSNP01261, and DBSNP07427 and other markers that are linked to at least one of the foregoing QTL markers, may be included in a plurality of marker loci to be selected or identified in a plant or germplasm.

In aspects of some embodiments, the resistance to blackleg of a canola plant can be quantitated using any suitable means or method known in the art.

I. II. Abbreviations

| | |
|---|---|
| AFLP | amplified fragment length polymorphism |
| ASH | allele specific hybridization |
| CCD | charge coupling device |
| EST | expressed sequence tag |
| FAME | fatty acid methyl ester |
| FID | flame ionization detector |
| GC | gas chromatography |
| LCR | ligase chain reaction |
| LG | linkage group |
| LNA | locked nucleic acid |
| LOD | logarithm (base 10) of odds |
| MAS | marker-assisted selection |
| NASBA | nucleic acid sequence based amplification |
| NIR | near infrared (spectroscopy) |
| NMR | nuclear magnetic resonance (spectroscopy) |
| ORF | open reading frame |
| PCR | polymerase chain reaction |
| PNA | peptide nucleic acid |
| QTL | quantitative trait locus |
| RAPD | randomly amplified polymorphic DNA |
| RFLP | restriction fragment length polymorphism |
| RT-PCR | reverse transcriptase-PCR |
| SNP | single nucleotide polymorphism |
| SSCP | single-strand conformation polymorphism |
| SSR | simple sequence repeat |

Terms

As used in this application, including the claims, terms in the singular and the singular forms, "a," "an," and "the," for example, include plural referents, unless the content clearly dictates otherwise. Thus, for example, a reference to "plant," "the plant," or "a plant" also refers to a plurality of plants. Furthermore, depending on the context, use of the term, "plant," may also refer to genetically-similar or identical progeny of that plant. Similarly, the term, "nucleic acid," may refer to many copies of a nucleic acid molecule. Likewise, the term, "probe," may refer to many similar or identical probe molecules.

Numeric ranges are inclusive of the numbers defining the range, and include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Mapping population: As used herein, the term "mapping population" may refer to a plant population (e.g., a canola plant population) used for gene mapping. Mapping populations are typically obtained from controlled crosses of parent genotypes, as may be provided by two inbred lines. Decisions on the selection of parents, mating design for the development of a mapping population, and the type of markers used depend upon the gene to be mapped, the availability of markers, and the molecular map. The parents of plants within a mapping population should have sufficient variation for a trait(s) of interest at both the nucleic acid sequence and phenotype level. Variation of the parents' nucleic acid sequence is used to trace recombination events in the plants of the mapping population. The availability of informative polymorphic markers is dependent upon the amount of nucleic acid sequence variation. Thus, informative markers may not be identified in particular crosses of parent genotypes, though such markers may exist.

A "genetic map" is a description of genetic linkage relationships among loci on one or more chromosomes (or linkage groups) within a given species, as may be determined by analysis of a mapping population. In some examples, a genetic map may be depicted in a diagrammatic or tabular form. The term "genetic mapping" may refer to the process of defining the linkage relationships of loci through the use of genetic markers, mapping populations segregating for the markers, and standard genetic principles of recombination frequency. A "genetic map location" refers to a location on a genetic map (relative to surrounding genetic markers on the same linkage group or chromosome) where a particular marker can be found within a given species. In contrast, a "physical map of the genome" refers to absolute distances (for example, measured in base pairs or isolated and overlapping contiguous genetic fragments) between markers within a given species. A physical map of the genome does not necessarily reflect the actual recombination frequencies observed in a test cross of a species between different points on the physical map.

Cross: As used herein, the term "cross" or "crossed" refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Introgression: As used herein, the term "introgression" refers to the transmission of an allele at a genetic locus into a genetic background. In some embodiments, introgression of a specific allele form at the locus may occur by transmitting the allele form to at least one progeny via a sexual cross between two parents of the same species, where at least one of the parents has the specific allele form in its genome. Progeny comprising the specific allele form may be repeatedly backcrossed to a line having a desired genetic background. Backcross progeny may be selected for the specific allele form, so as to produce a new variety wherein the specific allele form has been fixed in the genetic background. In some embodiments, introgression of a specific allele form may occur by recombination between two donor genomes (e.g., in a fused protoplast), where at least one of the donor genomes has the specific allele form in its genome. Introgression may involve transmission of a specific allele form that may be, for example and without limitation, a selected allele form of a marker allele; a QTL; and/or a transgene.

Germplasm: As used herein, the term "germplasm" refers to genetic material of or from an individual plant, a group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells).

As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated. In embodiments, a germplasm utilized in a method or plant as described herein is from a canola line or variety. In particular examples, a germplasm is seed of the canola line or variety. In particular examples, a germplasm is a nucleic acid sample from the canola line or variety.

Gene: As used herein, the term "gene" (or "genetic element") may refer to a heritable genomic DNA sequence with functional significance. The term "gene" may also be used to refer to, for example and without limitation, a cDNA and/or an mRNA encoded by a heritable genomic DNA sequence.

Genotype: As used herein, the term "genotype" refers to the genetic constitution of an individual (or group of individuals) at one or more particular loci. The genotype of an individual or group of individuals is defined and described by the allele forms at the one or more loci that the individual has inherited from its parents. The term genotype may also be used to refer to an individual's genetic constitution at a single locus, at multiple loci, or at all the loci in its genome. A "haplotype" is the genotype of an individual at a plurality of genetic loci. In some examples, the genetic loci described by a haplotype may be physically and genetically linked; i.e., the loci may be positioned on the same chromosome segment.

Quantitative trait locus: Specific chromosomal loci (or intervals) may be mapped in an organism's genome that correlates with particular quantitative phenotypes. Such loci are termed quantitative trait loci, or QTL. As used herein, the term "quantitative trait locus" (QTL) may refer to stretches of DNA that have been identified as likely DNA sequences (e.g., genes, non-coding sequences, and/or intergenic sequences) that underlie a quantitative trait, or phenotype, that varies in degree, and can be attributed to the interactions between two or more DNA sequences (e.g., genes, non-coding sequences, and/or intergenic sequences) or their expression products and their environment. Thus, the term "quantitative trait locus" includes polymorphic genetic loci with at least two alleles that differentially affect the expression of a phenotypic trait in at least one genetic background (e.g., in at least one breeding population or progeny). In practice, QTLs can be molecularly identified to help map regions of the genome that contain sequences involved in specifying a quantitative trait, such as blackleg resistance.

As used herein, the term "QTL interval" may refer to stretches of DNA that are linked to the genes that underlie the QTL trait. A QTL interval is typically, but not necessarily, larger than the QTL itself. A QTL interval may contain stretches of DNA that are 5' and/or 3' with respect to the QTL.

Multiple experimental paradigms have been developed to identify and analyze QTLs. See, e.g., Jansen (1996) Trends Plant Sci 1:89. The majority of published reports on QTL mapping in crop species have been based on the use of a bi-parental cross (Lynch and Walsh (1997) *Genetics and Analysis of Quantitative Traits*, Sinauer Associates, Sunderland). Typically, these paradigms involve crossing one or more parental pairs that can be, for example, a single pair derived from two inbred strains, or multiple related or unrelated parents of different inbred strains or lines, which each exhibit different characteristics relative to the phenotypic trait of interest. Typically, this experimental protocol involves deriving 100 to 300 segregating progeny from a single cross of two divergent inbred lines that are, for example, selected to maximize phenotypic and molecular marker differences between the lines. The parents and segregating progeny are genotyped for multiple marker loci, and evaluated for one to several quantitative traits (e.g., disease resistance). QTLs are then identified as significant statistical associations between genotypic values and phenotypic variability among the segregating progeny. The strength of this experimental protocol comes from the utilization of the inbred cross, because the resulting $F_1$ parents all have the same linkage phase (how the alleles were joined in the parental generation). Thus, after selfing of $F_1$ plants, all segregating $F_2$ progeny are informative and linkage disequilibrium is maximized, the linkage phase is known, there are only two QTL alleles, and (except for backcross progeny) the frequency of each QTL allele is 0.5.

Numerous statistical methods for determining whether markers are genetically linked to a QTL (or to another marker) are known to those of skill in the art and include, for example and without limitation, standard linear models, such as ANOVA or regression mapping (Haley and Knott (1992) Heredity 69:315); and maximum likelihood methods, such as expectation-maximization algorithms (e.g., Lander and Botstein (1989) Genetics 121:185-99; Jansen (1992) Theor. Appl. Genet. 85:252-60; Jansen (1993) Biometrics 49:227-31; Jansen (1994) "Mapping of quantitative trait loci by using genetic markers: an overview of biometrical models," In J. W. van Ooijen and J. Jansen (eds.), *Biometrics in Plant breeding: applications of molecular markers*, pp. 116-24, CPRO-DLO Metherlands; Jansen (1996) Genetics 142:305-11; and Jansen and Stam (1994) Genetics 136: 1447-55).

Exemplary statistical methods include single point marker analysis; interval mapping (Lander and Botstein (1989) Genetics 121:185); composite interval mapping; penalized regression analysis; complex pedigree analysis; MCMC analysis; MQM analysis (Jansen (1994) Genetics 138:871); HAPLO-IM+ analysis, HAPLO-MQM analysis, and HAPLO-MQM+ analysis; Bayesian MCMC; ridge regression; identity-by-descent analysis; and Haseman-Elston regression, any of which are suitable in the context of particular embodiments of the invention. Alternative statistical methods applicable to complex breeding populations that may be used to identify and localize QTLs in particular examples are described in U.S. Pat. No. 6,399,855 and PCT International Patent Publication No. WO0149104 A2. All of these approaches are computationally intensive and are usually performed with the assistance of a computer based system and specialized software. Appropriate statistical packages are available from a variety of public and commercial sources, and are known to those of skill in the art.

Marker: Although specific DNA sequences that encode proteins are generally well-conserved across a species, other regions of DNA (e.g., non-coding DNA and introns) tend to develop and accumulate polymorphism, and therefore, may be variable between individuals of the same species. The genomic variability can be of any origin, for example, the variability may be due to DNA insertions, deletions, duplications, repetitive DNA elements, point mutations, recombination events, and the presence and sequence of transposable elements. Such regions may contain useful molecular genetic markers. In general, any differentially inherited polymorphic trait (including nucleic acid polymorphisms) that segregates among progeny is a potential marker.

As used herein, the terms "marker" and "molecular marker" refer to a nucleotide sequence or encoded product thereof (e.g., a protein) used as a point of reference when identifying a linked locus. Thus, a marker may refer to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" or "marker allele form" refers to the version of the marker that is present in a particular individual. The term "marker" as used herein may refer to a cloned segment of chromosomal DNA, and may also or alternatively refer to a DNA molecule that is complementary to a cloned segment of chromosomal DNA. The term also refers to nucleic acid sequences complementary to genomic marker sequences, such as nucleic acid primers and probes.

A marker may be described, for example, as a specific polymorphic genetic element at a specific location in the genetic map of an organism. A genetic map may be a graphical representation of a genome (or a portion of a genome, such as a single chromosome) where the distances between landmarks on the chromosome are measured by the recombination frequencies between the landmarks. A genetic landmark can be any of a variety of known polymorphic markers, for example and without limitation: simple sequence repeat (SSR) markers; restriction fragment length polymorphism (RFLP) markers; and single nucleotide polymorphism (SNP) markers. As one example, SSR markers can be derived from genomic or expressed nucleic acids (e.g., expressed sequence tags (ESTs)).

Additional markers include, for example and without limitation, ESTs; amplified fragment length polymorphisms (AFLPs) (Vos et al. (1995) Nucl. Acids Res. 23:4407; Becker et al. (1995) Mol. Gen. Genet. 249:65; Meksem et al. (1995) Mol. Gen. Genet. 249:74); randomly amplified polymorphic DNA (RAPD), and isozyme markers. Isozyme markers may be employed as genetic markers, for example, to track isozyme markers or other types of markers that are linked to a particular first marker. Isozymes are multiple forms of enzymes that differ from one another with respect to amino acid sequence (and therefore with respect to their encoding nucleic acid sequences). Some isozymes are multimeric enzymes containing slightly different subunits. Other isozymes are either multimeric or monomeric, but have been cleaved from a pro-enzyme at different sites in the pro-enzyme amino acid sequence. Isozymes may be characterized and analyzed at the protein level or at the nucleic acid level. Thus, any of the nucleic acid based methods described herein can be used to analyze isozyme markers in particular examples.

"Genetic markers" include alleles that are polymorphic in a population, where the alleles of may be detected and distinguished by one or more analytic methods (e.g., RFLP analysis, AFLP analysis, isozyme marker analysis, SNP analysis, and SSR analysis). The term "genetic marker" may also refer to a genetic locus (a "marker locus") that may be used as a point of reference when identifying a genetically linked locus (e.g., QTL). Such a marker may also be referred to as a "QTL marker."

The nature of the foregoing physical landmarks (and the methods used to detect them) vary, but all of these markers are physically distinguishable from each other (as well as from the plurality of alleles of any one particular marker) on the basis of polynucleotide length and/or sequence. Numerous methods for detecting molecular markers and identifying marker alleles are well-established. A wide range of protocols are known to one of skill in the art for detecting this variability, and these protocols are frequently specific for the type of polymorphism they are designed to detect. Such protocols include, for example and without limitation, PCR amplification; detection of single-strand conformation polymorphism (SSCP), e.g., via electrophoresis; and self-sustained sequence replication (3SR) (see Chan and Fox (1999) Reviews in Medical Microbiology 10:185-96).

The primary motivation for developing molecular marker technologies from the perspective of plant breeders has been to increase breeding efficiency through MAS. A molecular marker allele that demonstrates linkage disequilibrium with a desired phenotypic trait (e.g., a QTL) provides a useful tool for the selection of the desired trait in a plant population. The key components to the implementation of an MAS approach are the creation of a dense (information rich) genetic map of molecular markers in the plant germplasm; the detection of at least one QTL based on statistical associations between marker and phenotypic variability; the definition of a set of particular useful marker alleles based on the results of the QTL analysis; and the use and/or extrapolation of this information to the current set of breeding germplasm to enable marker-based selection decisions to be made.

Genetic variability, for example as determined in a mapping population, may be observed between different populations of the same species (e.g., canola). In spite of the variability in the genetic map that may occur between populations of the same species, genetic map and marker information derived from one population generally remains useful across multiple populations for the purposes of identification and/or selection of plants and/or germplasm comprising traits that are linked to the markers and counter-selection of plants and/or germplasm comprising undesirable traits.

Two types of markers used in particular MAS protocols described herein are SSR and SNP markers. SSR markers include any type of molecular heterogeneity that results in nucleic acid sequence length variability. Exemplary SSR markers are short (up to several hundred base pairs) segments of DNA that consist of multiple tandem repeats of a short (ie, between two and ten) base-pair sequence. The repeated sequences, therefore, could be two, three, four, five, six, seven, eight, nine, or ten base pairs long. These repeated sequences result in highly polymorphic DNA regions of variable length due to poor replication fidelity (e.g., by polymerase slippage). SSRs appear to be randomly dispersed through the genome, and are generally flanked by conserved regions. SSR markers may also be derived from genic sequences (in the form of a cDNA, a partial cDNA, or an EST), as well as non-genic material.

The heterogeneity of SSR markers make them well-suited for use as molecular genetic markers. For example, SSR genomic variability is inherited, and it is multi-allelic, co-dominant, and reproducibly detectable. The proliferation of increasingly sophisticated amplification-based detection techniques (e.g., PCR-based techniques) provides a variety of sensitive methods for the detection of nucleotide sequence heterogeneity between samples. Probes (e.g., nucleic acid primers) may be designed to hybridize to conserved regions that flank the SSR, and the probes may be used to amplify the variable SSR region. The differently sized amplicons generated from an SSR region have characteristic and reproducible sizes. Differently sized SSR amplicons observed from two homologous chromosomes from an individual, or from different individuals, in the plant population define SSR marker alleles. As long as there exist at least two SSR marker alleles that produce PCR products with different sizes, the SSR may be employed as a marker.

Linkage (dis)equilibrium: As used herein, the term "linkage equilibrium" refers to the situation where two markers independently segregate; i.e., the markers sort randomly among progeny. Markers that show linkage equilibrium are considered unlinked (whether or not they lie on the same chromosome). As used herein, the term "linkage disequilibrium" refers to the situation where two markers segregate in a non-random manner; i.e., the markers have a recombination frequency of less than 50% (and thus by definition, are separated by less than 50 cM on the same linkage group). In some examples, markers that show linkage disequilibrium are considered linked.

Linked, tightly linked, and extremely tightly linked: As used herein, linkage between genes or markers may refer to the phenomenon in which genes or markers on a chromosome show a measurable probability of being passed on together to individuals in the next generation. Thus, linkage of one marker to another marker or gene may be measured and/or expressed as a recombination frequency. The closer two genes or markers are to each other, the closer to "1" this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance), the more tightly they are linked Because chromosomal distance is approximately proportional to the frequency of recombination events between traits, there is an approximate physical distance that correlates with recombination frequency. For example, in canola, 1 cM correlates, on average, to about 400 kb.

Thus, the term "linked" may refer herein to one or more genes or markers that are physically located within about 4.0 Mb of one another on the same canola chromosome (i.e., about 10 cM). Thus, two "linked" genes or markers may be separated by 4.1 Mb; about 4.0 Mb; about 3.0 Mb; about 2.5 Mb; 2.1 Mb; 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb; about 1.10 Mb; about 1.05 Mb; about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb; about 0.25 Mb; about 0.20 Mb; about 0.15 Mb; about 0.10 Mb; about 0.05 Mb; about 0.025 Mb; and about 0.01 Mb.

As used herein, the term "tightly-linked" may refer to one or more genes or markers that are located within about 2.0 Mb of one another on the same chromosome. Thus, two "tightly-linked" genes or markers may be separated by 2.1 Mb; about 1.75 Mb; about 1.5 Mb; about 1.0 Mb; about 0.9 Mb; about 0.8 Mb; about 0.7 Mb; about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.1 Mb; and about 0.05 Mb.

As used herein, the term "extremely tightly-linked" may refer to one or more genes or markers that are located within about 500 kb of one another on the same chromosome. Thus, two "extremely tightly-linked" genes or markers may be separated by 600 kb; about 450 kb; about 400 kb; about 350 kb; about 300 kb; about 250 kb; about 200 kb; about 175 kb; about 150 kb; about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 10 kb; about 5 kb; and about 1 kb.

The closer a particular marker is to a gene that encodes a polypeptide that contributes to a particular phenotype (whether measured in terms of genetic or physical distance), the more tightly-linked is the particular marker to the phenotype. In view of the foregoing, it will be appreciated that markers linked to a particular gene or phenotype include those markers that are tightly linked, and those markers that are extremely tightly linked, to the gene or phenotype. In some embodiments, the closer a particular marker is to a gene that encodes a polypeptide that contributes to a blackleg resistance phenotype (whether measured in terms of genetic or physical distance), the more tightly-linked is the particular marker to the blackleg resistance phenotype. Thus, linked, tightly linked, and extremely tightly genetic markers of a blackleg resistance phenotype in canola may be useful in MAS programs to identify canola varieties comprising improved blackleg resistance (when compared to parental varieties and/or at least one particular conventional variety), to identify individual canola plants comprising blackleg resistance (or improved blackleg resistance), and to breed this trait into other canola varieties to introduce or improve blackleg resistance.

In some embodiments, the linkage relationship between a molecular marker and a phenotype may be expressed as a "probability" or "adjusted probability." Within this context, a probability value is the statistical likelihood that a particular combination of a phenotype and the presence or absence of a particular marker allele form is random. Thus, the lower the probability score, the greater the likelihood that the phenotype and the particular marker allele form will co-segregate. In some examples, the probability score may be described as "significant" or "non-significant." In particular examples, a probability score of 0.05 (p=0.05 (a 5% probability)) of random assortment is considered a "significant" indication of co-segregation. However, a significant probability may in other examples be any probability of less than 50% (p=0.5). For instance, a significant probability may be less than 0.25; less than 0.20; less than 0.15; or less than 0.1.

In some embodiments, a marker that is linked to a blackleg resistance phenotype may be selected from the QTL markers of canola linkage group N10 that are illustrated in FIG. 2. In some embodiments, a marker that is linked to a blackleg resistance phenotype may be selected from those markers that are located within about 10 cM of a QTL marker illustrated in FIG. 2. Thus, marker that is linked to a blackleg resistance phenotype may be, for example, within 10 cM; 9 cM; 8 cM; 7 cM; 6 cM; 5 cM; 4 cM; 3 cM; 2 cM; 1 cM; 0.75 cM; 0.5 cM; 0.25 cM; or less, from a QTL marker illustrated in FIG. 2.

A plant breeder can advantageously use molecular markers to identify desired individuals by identifying marker alleles that show a statistically significant probability of co-segregation with a desired phenotype (e.g., blackleg resistance), manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select the phenotype by selecting for the proper molecular marker allele (i.e., MAS). The more molecular markers that are placed on the genetic map, the more potentially useful that map becomes for conducting MAS.

Marker set: As used herein, a "set" of markers or probes refers to a specific collection of markers or probes (or data derived therefrom) that may be used to identify individuals comprising a trait of interest. In some embodiments, a set of markers linked to the blackleg resistance phenotype may be used to identify canola plants comprising blackleg resistance. Data corresponding to a marker set or probe set (or data derived from the use of such markers or probes) may be stored in an electronic medium. While each marker in a marker set may possess utility with respect to trait identification, individual markers selected from the set and subsets including some, but not all, of the markers may also be effective in identifying individuals comprising the trait of interest.

Allele: As used herein, the term "allele" refers to one of two or more different nucleotide sequences that occur at a specific locus. For example, a first allele may occur on one chromosome, while a second allele may occur on a second homologous chromosome; e.g., as occurs for different chromosomes of a heterozygous individual, or between different homozygous or heterozygous individuals in a population. In some embodiments, a particular allele at a particular locus may be linked to an agronomically desirable phenotype (e.g., blackleg resistance). In some embodiments, a particular allele at the locus may allow the identification of plants that do not comprise the agronomically desirable phenotype (e.g., blackleg susceptibility) such that those plants may be removed from a breeding program or planting. A marker allele may segregate with a favorable phenotype, therefore providing the benefit of identifying plants comprising the phenotype. An "allelic form of a chromosome segment" may refer to a chromosome segment that comprises a marker allele nucleotide sequence that contributes to, or is linked to, a particular phenotype at one or more genetic loci physically located on the chromosome segment.

"Allele frequency" may refer to the frequency (expressed as a proportion or percentage) at which an allele is present at a locus within a plant, within a line, or within a population of lines. Thus, for an allele "A," a diploid individual of genotype "AA," "Aa," or "aa," has an allele frequency of 1.0, 0.5, or 0.0, respectively. The allele frequency within a line may be estimated by averaging the allele frequencies of a sample of individuals from that line. Similarly, the allele frequency within a population of lines may be calculated by averaging the allele frequencies of lines that make up the population. For a population with a finite number of individuals or lines, an allele frequency may be expressed as a count of individuals or lines (or any other specified grouping) containing the allele.

A marker allele "positively" correlates with a trait when the marker is linked to the trait, and when presence of the marker allele is an indicator that the desired trait or trait form will occur in a plant comprising the allele. A marker allele "negatively" correlates with a trait when the marker is linked to the trait, and when presence of the marker allele is an indicator that the desired trait or trait form will not occur in a plant comprising the allele.

A "homozygous" individual has only one form of allele at a given locus (e.g., a diploid plant has a copy of the same allele form at a particular locus for each of two homologous chromosomes). An individual is "heterozygous" if more than one allele form is present at the locus (e.g., a diploid individual has one copy of a first allele form and one copy of a second allele form at the locus). The term "homogeneity" refers to members of a group that have the same genotype (i.e., the same allele frequency) at one or more specific loci of interest. In contrast, the term "heterogeneity" refers to individuals within a group that differ in genotype at one or more specific loci of interest.

Any technique that may be used to characterize the nucleotide sequence at a locus may be used to identify a marker allele. Methods for marker allele detection include, for example and without limitation, molecular identification methods (e.g., amplification and detection of a marker amplicon). For example, an allelic form of an SSR marker, or of a SNP marker, may be detected by an amplification based technology. In a typical amplification-based detection method, a marker locus or a portion of the marker locus is amplified (using, e.g., PCR, LCR, and transcription using a nucleic acid isolated from a canola plant of interest as an amplification template), and the resulting amplified marker amplicon is detected. In some embodiments, plant RNA may be utilized as the template for an amplification reaction. In some embodiments, plant genomic DNA may be utilized as the template for the amplification reaction. In some examples, the QTL marker is an SNP marker, and the detected allele is a SNP marker allele, and the method of detection is allele specific hybridization (ASH). In some examples, the QTL marker is an SSR marker, and the detected allele is an SSR marker allele.

ASH technology is based on the stable annealing of a short, single-stranded, oligonucleotide probe to a completely complementary single-strand target nucleic acid. Detection may be accomplished via detection of an isotopic or non-isotopic label attached to the probe. For each polymorphism, two or more different ASH probes may be designed to have identical DNA sequences, except at site of a polymorphism. Each probe may be perfectly homologous with one allele sequence, so that the range of probes can distinguish all the known alternative allele sequences. When each probe is hybridized to target DNA under appropriate probe design and hybridization conditions, a single-base mismatch between the probe and target DNA prevents hybridization. In this manner, only one of the alternative probes will hybridize to a target sample that is homozygous for an allele. Samples that are heterozygous or heterogeneous for two alleles will hybridize to both of two alternative probes.

ASH markers may be used as dominant markers, where the presence or absence of only one allele is determined from hybridization or lack of hybridization by only one probe. The alternative allele may be inferred from a lack of hybridization. In examples, ASH probe and target molecules may be RNA or DNA molecules; a target molecule may comprise any length of nucleotides beyond the sequence that is complementary to the probe; the probe may be designed to hybridize with either strand of a DNA target; and the size of the probe may be varied to conform with the requirements of different hybridization conditions.

Amplified variable sequences refer to amplified sequences of the plant genome that exhibit high nucleic acid residue variability between members of the same species. All organisms have variable genomic sequences, and each organism (with the exception of a clone) has a different set of variable sequences. Once identified, the presence of specific variable sequence can be used to predict phenotypic traits. DNA from a plant may in some examples be used as a template for amplification with primers that flank a variable sequence of DNA. The variable sequence may be amplified and then sequenced.

Self-sustained sequence replication may also and alternatively be used to identify genetic markers. Self-sustained sequence replication refers to a method of nucleic acid amplification using target nucleic acid sequences that are replicated exponentially in vitro under substantially isothermal conditions, using three enzymatic activities involved in retroviral replication: reverse transcriptase; Rnase H; and a DNA-dependent RNA polymerase. Guatelli et al. (1990) Proc. Natl. Acad. Sci. USA 87:1874. By mimicking the retroviral strategy of RNA replication by means of cDNA intermediates, this reaction accumulates cDNA and RNA copies of the original target.

Data representing detected marker allele(s) may be transmitted (for example, electronically; and via infrared, wireless, or optical transmission) to a computer or computer-readable medium for analysis or storage.

For example, an amplification primer or amplification primer pair may be admixed with a genomic nucleic acid isolated from a first canola plant or germplasm, wherein the primer or primer pair is complementary or partially complementary to at least a portion of a marker locus, and the primer or primer pair is capable of initiating DNA polymerization by a DNA polymerase using the canola genomic nucleic acid as a template. The primer or primer pair (e.g., a primer pair provided in Table 3 is extended in a DNA polymerization reaction utilizing a DNA polymerase and a template genomic nucleic acid to generate at least one amplicon.

"Positional cloning" refers to a particular cloning procedure in which a target nucleic acid is identified and isolated by its genomic proximity to a marker. For example, a genomic nucleic acid clone may include all or part of two more chromosomal regions that are proximal to one another. If a marker can be used to identify the genomic nucleic acid clone from a genomic library, standard methods such as sub-cloning and/or sequencing may be used to identify and or isolate sub-sequences of the clone that are located near the marker.

Locus: As used herein, the term "locus" refers to a position on the genome that corresponds to a measurable characteristic (e.g., a trait) or polymorphism. An SNP locus is defined by a probe that hybridizes to DNA contained within the locus.

Marker-assisted breeding: As used herein, the term "marker-assisted breeding" may refer to an approach to breeding directly utilizing MAS for one or more traits (e.g., improved blackleg resistance). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Probe: In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}$P. Other labels which may be used include, for example and without limitation: Fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait (e.g., blackleg resistance). For example, in some embodiments, a noncontiguous probe is located within about 10 cM; 9 cM; 8 cM; 7 cM; 6 cM; 5 cM; 4 cM; 3 cM; 2 cM; 1 cM; 0.75 cM; 0.5 cM; 0.25 cM; or less, from a QTL marker illustrated in FIG. 2

A probe may be an exact copy of a marker to be detected. A probe may also be a nucleic acid molecule comprising, or consisting of, a nucleotide sequence which is substantially identical to a cloned segment of the subject organism's (e.g., canola) chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to a reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

The following are representative, non-limiting hybridization conditions.

Very High Stringency (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

High Stringency (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency (detects sequences that share at least 50% sequence identity): Hybridization in 6×SSC buffer at room temperature to 55° C. for 16-20 hours; wash at least twice in 2×-3×SSC buffer at room temperature to 55° C. for 20-30 minutes each.

With respect to all probes discussed, supra, the probe may comprise additional nucleic acid sequences, for example, promoters; transcription signals; and/or vector sequences. Any of the probes discussed, supra, may be used to define additional markers that are linked to a gene involved blackleg resistance in canola, and markers thus identified may be equivalent to exemplary markers named in the present disclosure, and thus are within the scope of the invention.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

An "exogenous" molecule is a molecule that is not native to a specified system (e.g., a germplasm, variety, elite variety, and/or plant) with respect to nucleotide sequence and /or genomic location for a polynucleotide, and with respect to amino acid sequence and/or cellular localization for a polypeptide. In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

The term "recombinant" refers to a material (e.g., recombinant nucleic acid, recombinant gene, recombinant polynucleotide, and/or recombinant polypeptide) that has been altered by human intervention. For example, the arrangement of the parts or elements of a recombinant molecule may not be a native arrangement, and/or the primary sequence of the recombinant molecule may been changed from its native sequence in some way. A material may be altered to produce a recombinant material within or removed from its natural environment or state. An open reading frame of a nucleic acid is recombinant if the nucleotide sequence of the open reading frame has been removed from it natural context and cloned into any type of artificial nucleic acid (e.g., a vector). Protocols and reagents to produce recombinant molecules, especially recombinant nucleic acids, are common and routine in the art. The term "recombinant" may also herein refer to a cell or organism that comprises recombinant material (e.g., a plant and/or plant cell that comprises a recombinant nucleic acid). In some examples, a recombinant organism is a transgenic organism.

As used herein, the term "introduced," when referring to translocation of a heterologous or exogenous nucleic acid into a cell, refers to the incorporation of the nucleic acid into the cell using any methodology available in the art. This term encompasses nucleic acid introduction methods including, for example and without limitation, transfection; transformation; and transduction.

As used herein, the term "vector" refers to a polynucleotide or other molecules that is capable of transferring at least one nucleic acid segment(s) into a cell. A vector may optionally comprise components/elements that mediate vector maintenance and enable its intended use (e.g., sequences necessary for replication, genes imparting drug or antibiotic resistance, a multiple cloning site, and/or operably-linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably-linked elements to facilitate cloning or subcloning steps (e.g., a multiple cloning site containing multiple restriction endonuclease sites).

The term "expression vector," as used herein, refers to a vector comprising operably-linked polynucleotide sequences that may facilitate expression of a coding sequence in a particular host organism. For example, a bacterial expression vector may facilitate expression of a coding sequence in a bacterium. A plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) comprise promoters, enhancers, termination, and polyadenylation signals (and other sequences) that are generally different from those used in prokaryotic expression vectors.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, markers linked to SCN resistance are SNP markers.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant. Thus, the term "canola plant" may refer to, for example and without limitation, a whole canola plant; multiple canola plants; canola plant cell(s); canola plant protoplast; canola tissue culture (e.g., from which a canola plant can be regenerated); canola plant callus; canola plant parts (e.g., canola seed, canola flower, canola cotyledon, canola leaf, canola stem, canola bud, canola root, and canola root tip); and canola plant cells that are intact in canola plants or in parts of canola plants.

A "transgenic plant" is a plant comprising within at least one of its cells an exogenous polynucleotide. In examples, the exogenous polynucleotide is stably-integrated within the genome of the cell, such that the polynucleotide may be inherited in successive generations. In some examples, the heterologous polynucleotide may be integrated into the genome as part of a recombinant expression cassette. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally-occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci. A "subline" may refer to an inbred subset of descendents from a common progenitor that are genetically distinct from other similarly inbred subsets descended from the same progenitor. In some embodiments, a "subline" may be produced by inbreeding seed from an individual canola plant selected at the $F_3$ to $F_5$ generation until the residual segregating loci are homozygous across most or all loci.

Commercial canola varieties are typically produced by aggregating the self-pollinated progeny ("bulking") of a single $F_3$ to $F_5$ plant from a controlled cross between 2 genetically different parents. While such a variety typically appears uniform, a self-pollinating variety derived from the selected plant eventually (for example, by the $F_8$ generation) becomes a mixture of homozygous plants that may vary in genotype at any locus that was heterozygous in the originally selected $F_3$ to $F_5$ plant. In embodiments described herein, marker-based sublines that differ from each other based on qualitative marker polymorphism at the DNA level at one or more specific loci, are produced by genotyping a sample of seed derived from individual self-pollinated progeny derived from a selected $F_3$ to $F_5$ plant. Such a seed sample may be genotyped directly as seed, or as plant tissue grown from seed. In some examples, seed sharing a common genotype at one or more specified marker locus are bulked to produce a subline that is genetically homogenous at one or more locus that is linked to a trait of interest (e.g., blackleg resistance).

An "ancestral line" refers to a parent line that is or has been used as a source of genetic material, for example, for the development of elite lines. An "ancestral population" refers to a group of ancestors that have contributed the bulk of the genetic variation that was used to develop an elite line. "Descendants" are progeny of ancestors, and descendents may be separated from their ancestors by many generations of breeding. For example, elite lines are the descendants of their ancestors. A pedigree may be used to describe the relationship between a descendant and each of its ancestors. A pedigree may span one or more generations, and thus may describe relationships between a descendant and its ancestors removed by 1, 2, 3, 4, etc. generations.

An "elite line" or "elite strain" refers to an agronomically superior line that has been bred and selected (often through many cycles) for superior agronomic performance. Numerous elite canola lines are available and known to those of skill in the art. An elite population is an assortment of elite lines or individuals from elite lines that may be used to represent the state of the art in terms of the available agronomically superior genotypes of a given crop species (e.g., canola). Similarly, an elite germplasm or elite strain of germplasm is an agronomically superior germplasm. An elite germplasm may be obtained from a plant with superior agronomic performance, and may capable of being used to generate a plant with superior agronomic performance, such as a canola of an existing or newly-developed elite line.

In contrast to elite lines, an "exotic line" or "exotic strain" (or an "exotic germplasm") refers to a line or germplasm obtained from a canola not belonging to an available elite canola line or strain of germplasm. In the context of a cross between two canola plants or germplasms, an exotic germplasm is not closely related by descent to the elite germplasm with which it is crossed. Most commonly, exotic germplasm has been selected to introduce a novel genetic element (e.g., an allele form of interest) into a breeding program.

Trait or phenotype: The terms "trait" and "phenotype" are used interchangeably herein to refer to a measurable or observable heritable characteristic. A phenotype may in some examples be directly controlled by a single gene or genetic locus (i.e., a single gene trait). In other examples, a phenotype may be the result of an interaction between several genes (a complex trait). Thus, a QTL can act through a single gene mechanism or by a polygenic mechanism. In some examples, a trait or phenotype can be assigned a "phenotypic value," which corresponds to a quantitative value measured for the phenotypic trait.

The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Blackleg resistance: For the purposes of the present disclosure, a trait of particular interest is "blackleg resistance." Those in the art understand that blackleg resistance is predominantly determined by heritable genetic factors. Thus, for example, the selection of a particular canola variety for cultivation may be based at least in part on the characteristic disease (for instance, blackleg) resistance of that particular variety under normal field growing conditions (e.g., conditions without drought, disease, and adequate soil nutrients). In examples, a canola plant having a blackleg susceptibility may comprise a blackleg susceptibility rating of 0, 1, 3, 5, 7 or 9, (See Table 1), where a rating of 9 indicates great susceptibility, or limited resistance to, blackleg disease.

In some embodiments, "blackleg resistance" is determined by comparison with the characteristic blackleg resistance of a wild-type or parental variety. Thus, a first canola comprising a blackleg resistance phenotype may have "increased" or "greater" levels of blackleg resistance (or "decreased" or "lower" levels of blackleg susceptibility) relative to a wild-type canola, or relative to a parental canola variety from which the first canola was derived. Increased or greater are relative terms, indicating that the plant resists blackleg disease better, or to a greater degree, than a similar wild-type plant. Decreased and lowered are relative terms, indicating that the plant is more susceptible to blackleg disease or is susceptible to a greater degree, than a similar wild-type plant.

Description of how blackleg resistance rating is scored.
Detection of Markers for Blackleg Resistance in Canola Methods for detecting (identifying) canola plants or germplasm that carry particular alleles of blackleg resistance marker loci are a feature of some embodiments. In some embodiments, any of a variety of marker detection protocols available in the art may be used to detect a marker allele, depending on the type of marker being detected. In examples, suitable methods for marker detection may include amplification and identification of the resulting amplified marker by, for example and without limitation, PCR; LCR; and transcription-based amplification methods (e.g., ASH, SSR detection, RFLP analysis, and many others).

In general, a genetic marker relies on one or more property of nucleic acids for its detection. For example, some techniques for detecting genetic markers utilize hybridization of a probe nucleic acid to a nucleic acid corresponding to the genetic marker (e.g., an amplified nucleic acid produced using a genomic canola DNA molecule as a template). Hybridization formats including, for example and without limitation, solution phase; solid phase; mixed phase; and in situ hybridization assays may be useful for allele detection in particular embodiments. An extensive guide to the hybridization of nucleic acids may be found, for example, in Tijssen (1993) *Laboratory Techniques in Biochemistry and Molecular Biology- Hybridization with Nucleic Acid Probes* Elsevier, N.Y.

Markers corresponding to genetic polymorphisms between members of a population may be detected by any of numerous methods including, for example and without limitation, nucleic acid amplification-based methods; and nucleotide sequencing of a polymorphic marker region. Many detection methods (including amplification-based and sequencing-based methods) may be readily adapted to high throughput analysis in some examples, for example, by using available high throughput sequencing methods, such as sequencing by hybridization.

Amplification primers for amplifying SSR-type marker loci are included in particular examples of some embodiments. Table 6 provides specific primers for amplification of particular markers described herein. However, one of skill will immediately recognize that other sequences on either side of the given primers may be used in place of the given primers, so long as the primers are capable of amplifying a nucleotide sequence comprising the allele to be detected. Further, the precise probe used for allele detection may vary. For example, any probe capable of identifying the region of a marker amplicon to be detected may be substituted for the exemplary probes listed herein. Further, the configuration of amplification primers and detection probes may also vary. Thus, embodiments are not limited to the primers and probes specifically recited herein. Although many specific examples of primers are provided herein (see Table 6), suitable primers to be used with the invention may be designed using any suitable method. For example, equivalent primers may be designed using any suitable software program, such as for example and without limitation, LASERGENE®.

Molecular markers may be detected by established methods available in the art including, for example and without limitation: ASH, or other methods for detecting SNPs; AFLP detection; amplified variable sequence detection; RAPD detection; RFLP detection; self-sustained sequence replication detection; SSR detection; SSCP detection; and isozyme markers detection. While the exemplary markers provided in FIG. 1 and Table 6 are SSR markers, any of the aforementioned marker types may be employed in particular embodiments to identify chromosome segments encompassing a genetic element that contributes to a blackleg resistance phenotype in canola.

For example, markers that comprise RFLPs may be detected, for example, by hybridizing a probe (which is typically a sub-fragment or synthetic oligonucleotide corresponding to a sub-fragment) of the nucleic acid to be detected to restriction-digested genomic DNA. The restriction enzyme is selected so as to provide restriction fragments of at least two alternative (or polymorphic) lengths in different individuals or populations. Determining one or more restriction enzyme(s) that produces informative fragments for each cross is a simple procedure that is easily accomplished by those of skill in the art after provision of the target DNA sequence. After separation by length in an appropriate matrix (e.g., agarose or polyacrylamide) and transfer to a membrane (e.g., nitrocellulose or nylon), a labeled probe may be hybridized under conditions that result in equilibrium binding of the probe to the target, followed by removal of excess probe by washing, and detection of the labeled probe.

In some embodiments, an amplification step is utilized as part of a method to detect/genotype a marker locus. However, an amplification step is not in all cases a requirement for marker detection. For example, an unamplified genomic DNA may be detected simply by performing a Southern blot on a sample of genomic DNA. Separate detection probes may also be omitted in amplification/detection methods, for example and without limitation, by performing a real time amplification reaction that detects product formation by modification of an amplification primer upon incorporation into a product; incorporation of labeled nucleotides into an amplicon; and by monitoring changes in molecular rotation properties of amplicons as compared to unamplified precursors (e.g., by fluorescence polarization).

PCR, RT-PCR, real-time PCR, and LCR are in particularly broad use as amplification and amplification-detection methods for amplifying and detecting nucleic acids (e.g., those comprising marker loci). Details regarding the use of these and other amplification methods can be found in any of a variety of standard texts including, for example, Sambrook et al., *Molecular Cloning—A Laboratory Manual* (2000) 3rd Ed., Vol. 1-3, Cold Spring Harbor Laboratory, Cold Spring Harbor, N.Y.; *Current Protocols in Molecular Biology*, (supplemented through 2002) F. M. Ausubel et al., eds., Current Protocols, a joint venture between Greene Publishing Associates, Inc. and John Wiley & Sons, Inc.; and *PCR Protocols A Guide to Methods and Applications* (1990) Innis et al. eds) Academic Press Inc., San Diego, Calif. Additional details regarding detection of nucleic acids in plants can also be found, for example, in *Plant Molecular Biology* (1993) Croy (ed.) BIOS Scientific Publishers, Inc.

Additional details regarding techniques sufficient to direct persons of skill through particular in vitro amplification and detection methods, including the polymerase chain reaction (PCR), the ligase chain reaction (LCR), Qβ-replicase amplification, and other RNA polymerase-mediated techniques (e.g., NASBA), and examples thereof, may also be found in, for example: U.S. Pat. No. 4,683,202; Arnheim and Levinson (1991) J. NIH Res. 3:81-94; Kwoh et al. (1989) Proc. Natl. Acad. Sci. USA 86:1173; Guatelli et al. (1990), supra; Lomell et al. (1989) J. Clin. Chem. 35:1826; Landegren et al. (1988) Science 241:1077-80; Van Brunt (1990) Biotechnology 8:291-4; Wu and Wallace (1989) Gene 4:560; Barringer et al. (1990) Gene 89:117; and Sooknanan and Malek (1995) Biotechnology 13:563-4. Improved methods of amplifying large nucleic acids by PCR, which may be useful in some applications of positional cloning, are further described in Cheng et al. (1994) Nature 369: 684, and the references cited therein, in which PCR amplicons of up to 40 kb are generated.

Many available biology texts also have extended discussions regarding PCR and related amplification methods. One of skill will appreciate that essentially any RNA can be converted into a double-stranded DNA that is suitable for restriction digestion, PCR amplification, and sequencing using reverse transcriptase and a polymerase (e.g., by RT-PCR).

In some embodiments, a nucleic acid probe may be used to detect a nucleic acid that comprises a marker allele nucleotide sequence. Such probes can be used, for example, in positional cloning to isolate nucleotide sequences that are linked to a marker allele sequence. Nucleic acid probes that are useful in particular embodiments are not limited by any particular size constraint. In some embodiments, a nucleic acid probe may be, for example and without limitation, at least 20 nucleotides in length; at least 50 nucleotides in length; at least 100 nucleotides in length; and at least 200 nucleotides in length. Nucleic acid probes to a marker locus may be cloned and/or synthesized.

Any suitable label may be used with a probe in particular examples. Detectable labels suitable for use with nucleic acid probes include any composition detectable by spectroscopic, radioisotopic, photochemical, biochemical, immunochemical, electrical, optical, or chemical means. Thus, a hybridized probe may be detected using, for example, autoradiography, fluorography, or other similar detection techniques, depending on the particular label to be detected. Useful labels include biotin (for staining with labeled streptavidin conjugate), magnetic beads, fluorescent dyes, radiolabels, enzymes, and colorimetric labels. Other labels include ligands that bind to antibodies or specific binding targets labeled with fluorophores, chemiluminescent agents, and enzymes. A probe may also comprise radiolabelled PCR primers that are used to generate a radiolabelled amplicon. Additional information regarding labeling strategies for labeling nucleic acids, and corresponding detection strategies may be found, for example, in Haugland (1996) *Handbook of Fluorescent Probes and Research Chemicals, Sixth Edition*, Molecular Probes, Inc., Eugene Oreg.; and Haugland (2001) *Handbook of Fluorescent Probes and Research Chemicals, Eighth Edition*, Molecular Probes, Inc., Eugene, Oreg. (Available on CD ROM). In particular examples, PCR detection and quantification is carried out using dual-labeled fluorogenic oligonucleotide probes, for example, TaqMan® probes (Applied Biosystems).

In some embodiments, primers are not labeled, and marker PCR amplicons may be visualized, for example, following their size resolution (e.g., following agarose gel electrophoresis). In particular examples, ethidium bromide staining of PCR amplicons following size resolution allows visualization of differently size amplicons corresponding to different marker alleles.

Primers for use in embodiments are not limited to those capable of generating an amplicon of any particular size. For example, primers used to amplify particular marker loci and alleles are not limited to those amplifying the entire region of the relevant locus. The primers may generate an amplicon of any suitable length that is longer or shorter than those given in the allele definitions. In examples, marker amplification may produce an amplicon that is, for example and without limitation, at least 20 nucleotides in length; at least 50 nucleotides in length; at least 100 nucleotides in length; and at least 200 nucleotides in length.

Synthetic methods for making oligonucleotides and useful compositions comprising oligonucleotides (e.g., probes, primers, molecular beacons, PNAs, and LNAs) are generally well-known by those of skill in the art. For example, oligonucleotides may be synthesized chemically according to the solid phase phosphoramidite triester method described in, for example, Beaucage and Caruthers (1981) Tetrahedron Letts. 22(20):1859-62. Such methods may employ an automated synthesizer, for example and without limitation, as described in Needham-VanDevanter et al. (1984) Nucleic Acids Res. 12:6159-68. Oligonucleotides (including modified oligonucleotides) may also be ordered from a variety of commercial sources including, for example and without limitation, The Midland Certified Reagent Company; The Great American Gene Company; ExpressGen Inc.; and Operon Technologies Inc. Similarly, PNAs may be custom ordered from any of a variety of sources including, for example and without limitation, PeptidoGenic; HTI Bio-Products, Inc.; BMA Biomedicals Ltd (U.K.); and Bio.Synthesis, Inc.

In some embodiments, an in silico method may be used to detect a marker allele. For example, the sequence of a nucleic acid comprising a marker sequence may be stored in a computer. The desired marker locus sequence (or its homolog) may be identified using an appropriate nucleic acid search algorithm, as provided by, for example and without limitation, BLAST™, or even simple word processors.

In some embodiments, a marker allele is detected using a PCR-based detection method, where the size or sequence of a PCR amplicon comprising the marker is indicative of the absence or presence of a particular marker allele. In some examples, PCR primers are hybridized to conserved regions flanking the polymorphic marker region. PCR primers so used to amplify a molecular marker are sometimes referred to in the art as "PCR markers," or simply "markers."

A primary motivation for development of molecular markers in crop species is the potential for increased efficiency in plant breeding through marker assisted selection (MAS). Genetic markers that are linked to a trait or gene of interest may be used to identify plants that contain a desired marker allele at one or more loci, which plants are thus expected to transfer the desired marker allele, along with the trait or gene of interest, to their progeny. Genetic markers may be used to identify plants that contain a particular genotype at one locus, or at several unlinked or linked loci (e.g., a haplotype). Similarly, marker alleles described herein may be introgressed into any desired canola genetic background, germplasm, plant, line, variety, etc., as part of an overall MAS breeding program designed to enhance canola yield.

According to some embodiments, markers described herein provide the means to identify canola plants and germplasm that comprise blackleg resistance (or increased blackleg resistance, or decreased blackleg susceptibility) by identifying plants and germplasm comprising a specific allele at a locus such as DBSNP09246, DBSNP01407, DBSNP05863, DBSNP01261, and/or a marker locus linked to at least one of the foregoing. By identifying plants lacking a marker allele that co-segregates with blackleg resistance, blackleg susceptible plants and germplasm (or plants with a lesser degree of blackleg resistance) may be identified, for example, for elimination from subsequent crosses and breeding.

According to the foregoing, embodiments of the invention include molecular markers that have a significant probability of co-segregation with a QTL that contributes to or imparts a blackleg resistance phenotype. These QTL markers find use in marker assisted selection for desired traits (blackleg resistance), and also have other uses. Embodiments of the invention are not limited to any particular method for the detection or analysis of these markers.

Introgression of Markers for Blackleg Resistance into Canola Lines

As set forth, supra, identification of canola plants or germplasm that includes a marker allele or alleles that is/are linked to blackleg resistant phenotype provides a basis for performing marker assisted selection of canola. In some embodiments, at least one canola plant that comprises at least one marker allele that is positively correlated blackleg resistance is selected, while canola plants that comprise marker alleles that are negatively correlated with blackleg resistance may be selected against.

Desired marker alleles that are positively correlated blackleg resistance may be introgressed into canola having a particular (e.g., elite or exotic) genetic background, so as to produce an introgressed blackleg resistant canola plant or germplasm. In some embodiments, a plurality of blackleg resistance markers may be sequentially or simultaneous selected and/or introgressed into canola. The particular combinations of blackleg resistance markers that may be selected for in a single plant or germplasm is not limited, and can include a combination of markers such as those set forth in FIG. 2, any markers linked to the markers recited in FIG. 2, or any markers located within the QTL intervals defined herein.

In embodiments, the ability to identify QTL marker alleles that are positively correlated with blackleg resistance of a canola plant provides a method for selecting plants that have favorable marker loci as well. For example, any plant that is identified as comprising a desired marker allele (e.g., a marker allele that positively correlates with blackleg resistance) may be selected for, while plants that lack the allele (or that comprise an allele that negatively correlates with blackleg resistance) may be selected against. Thus, in particular embodiments, subsequent to identification of a marker allele in a first plant or germplasm, an introgression method includes selecting the first canola plant or germplasm, or selecting a progeny of the first plant or germplasm. In some examples, the resulting selected canola plant or germplasm may be crossed with a second canola plant or germplasm (e.g., an elite canola or an exotic canola), so as to produce progeny comprising the marker allele and desirable characteristics and/or alleles of the second plant or germplasm.

In some embodiments, a method of introgressing a blackleg resistance QTL may include, for example, providing at least one marker linked to blackleg resistance (e.g., a marker that co-segregates with blackleg resistance); determining the marker allele in a first plant or germplasm comprising blackleg resistance QTL; and introgressing the marker allele into a second canola plant or germplasm, so as to produce an introgressed canola plant or germplasm. In particular embodiments, the second canola plant or germplasm may comprise improved blackleg resistance as compared to the first canola plant or germplasm, while the introgressed canola plant or germplasm will comprise a blackleg resistance as compared to the second plant or germplasm. As discussed in more detail below, an introgressed canola plant or germplasm produced by these and other embodiments are also included in embodiments of the invention.

In some embodiments, where an introgressed canola plant or germplasm is produced by any of the methods provided herein, the introgressed canola plant or germplasm may be characterized by the blackleg susceptibility or resistance of the plant. An introgressed plant or germplasm may comprise, for example and without limitation, a blackleg susceptibility rating of 0, 1, 3, or 5. In some examples, such an introgressed canola plant or germplasm comprises a blackleg susceptibility rating of 0, 1, 3, 5, or 7.

In addition to introgressing selected marker alleles (e.g., through standard breeding methods) into desired genetic backgrounds, so as to introgress a blackleg resistance QTL into the background, transgenic approaches may be used in some embodiments to produce blackleg resistance canola plants and/or germplasm. In some embodiments, an exogenous nucleic acid (e.g., a gene or open reading frame) that is linked to at least one marker described herein in canola may be introduced into a target plant or germplasm. For example, a nucleic acid coding sequence linked to at least one marker described herein may be cloned from canola genomic DNA (e.g., via positional cloning) and introduced into a target plant or germplasm.

Thus, particular embodiments include methods for producing a canola plant or germplasm comprising a blackleg resistance phenotype, wherein the method comprises introducing an exogenous nucleic acid into a target canola plant or progeny thereof, wherein the exogenous nucleic acid is substantially identical to a nucleotide sequence that is linked to at least one positively-correlated marker allele at one or more marker locus that is linked to blackleg resistance. In some examples, the marker locus may be selected from: DBSNP02349, DBSNP09246, DBSNP01407, DBSNP05863, DBSNP01261, and DBSNP07427; and a marker that is linked (e.g., demonstrating not more than 10% recombination frequency) to at least one of the foregoing. In some embodiments, a plurality of linked markers may be used to construct a transgenic plant. Which of the markers described herein that are used in such a plurality is within the discretion of the practitioner.

Any of a variety of methods can be used to provide an exogenous nucleic acid to a canola plant or germplasm. In some embodiments, a nucleotide sequence is isolated by positional cloning, and is identified by linkage to a marker allele that is positively correlated with blackleg resistance. For example, the nucleotide sequence may correspond to an open reading frame (ORF) that encodes a polypeptide that, when expressed in a canola plant, results in or contributes to the canola plant having blackleg resistance. The nucleotide sequence may then be incorporated into an exogenous nucleic acid molecule. The precise composition of the exogenous nucleic acid may vary. For example, an exogenous nucleic acid may comprise an expression vector to provide for expression of the nucleotide sequence in the plant wherein the exogenous nucleic acid is introduced.

Markers linked to blackleg resistance may be introgressed (for example, thereby introgressing a blackleg resistance phenotype) into a canola plant or germplasm utilizing a method comprising marker assisted selection. In embodiments, MAS is performed using polymorphic markers that have been identified as having a significant likelihood of co-segregation with a blackleg resistance trait. Such markers (e.g., those set forth in FIG. 2) are presumed to map within or near a gene or genes that contribute to the blackleg resistance of the plant (compared to a plant comprising the wild-type gene or genes). Such markers may be considered indicators for the trait, and may be referred to as QTL markers. In embodiments, a plant or germplasm is tested for the presence of a positively correlated allele in at least one QTL marker.

In embodiments, linkage analysis is used to determine which polymorphic marker allele demonstrates a statistical likelihood of co-segregation with a blackleg resistance phenotype. Following identification of such a positively correlated marker allele for the blackleg resistance phenotype, the marker may then be used for rapid, accurate screening of plant lines for the blackleg resistance allele without the need to grow the plants through their life cycle and await phenotypic evaluations. Furthermore, the identification of the marker permits genetic selection for the particular blackleg resistance allele, even when the molecular identity of the actual blackleg resistance QTL is unknown. A small tissue sample (for example, from the first leaf of the plant) may be taken from a progeny canola plant produced by a cross and screened with the appropriate molecular marker. Thereby, it may be rapidly determined whether the progeny should be advanced for further breeding.

In some embodiments comprising MAS, a polymorphic QTL marker locus may be used to select a plant that contains a marker allele (or alleles) that is positively correlated with a blackleg resistance phenotype. For example, a nucleic acid corresponding to the marker nucleic acid allele may be detected in a biological sample from the plant to be selected. This detection may take the form of hybridization of a probe nucleic acid to a marker allele or amplicon thereof (e.g., using allele-specific hybridization, Southern analysis, northern analysis, in situ hybridization, and hybridization of primers followed by PCR amplification of a region of the marker). After the presence (or absence) of the particular marker allele in the biological sample is verified, the plant is selected, and may in some examples be used to make progeny plants by selective breeding.

Canola plant breeders desire combinations of blackleg resistance marker loci with markers/genes other desirable traits (e.g., high yield) to develop improved canola varieties. Screening large numbers of samples by non-molecular methods (e.g., trait evaluation in canola plants) is generally expensive, time consuming, and unreliable. Use of the polymorphic markers described herein, which are linked to blackleg resistance QTL, provides an effective method for selecting desirable varieties in breeding programs. Advantages of marker-assisted selection over field evaluations for blackleg resistance include, for example, that MAS can be done at any time of year, regardless of the growing season. Moreover, as set forth, supra, environmental effects are largely irrelevant to marker-assisted selection.

When a population is segregating for multiple marker loci linked to one or more traits (e.g., multiple markers linked to blackleg resistance), the efficiency of MAS compared to phenotypic screening becomes even greater, because all of the marker loci may be evaluated in the lab together from a single sample of DNA. In particular embodiments of the invention, the DBSNP02349, DBSNP09246, DBSNP01407, DBSNP05863, DBSNP01261, and DBSNP07427 markers, as well as markers linked to at least one of the foregoing, may be assayed simultaneously or sequentially from a single sample, or from a plurality of parallel samples.

Another use of MAS in plant breeding is to assist the recovery of the recurrent parent genotype by backcross breeding. Backcrossing is usually performed for the purpose of introgressing one or a few markers or QTL loci from a donor parent (e.g., a parent comprising desirable blackleg resistance marker loci) into an otherwise desirable genetic background from a recurrent parent (e.g., an otherwise high yielding canola line). The more cycles of backcrossing that are done, the greater the genetic contribution of the recurrent parent to the resulting introgressed variety. In some examples, many cycles of backcrossing may be carried out, for example, because blackleg resistance plants may be otherwise undesirable, e.g., due to low yield, low fecundity, etc. In contrast, strains which are the result of intensive breeding programs may have excellent yield, fecundity, etc., merely being deficient in one desirable respect, such as blackleg susceptibility. In marker assisted backcrossing of specific markers from a donor source, which may or may not constitute an elite genetic background to an elite variety that will serve as the recurrent line, the practitioner may select among backcross progeny for the donor marker, and then use repeated backcrossing to the recurrent line to reconstitute as much of the recurrent line's genome as possible.

According to the foregoing, markers and methods described herein may be utilized to guide marker assisted selection or breeding of canola varieties with the desired complement (set) of allelic forms of chromosome segments associated with superior agronomic performance (e.g., blackleg resistance, along with any other available markers for yield, disease resistance, etc.). Any of the described marker alleles may be introduced into a canola line via introgression (e.g., by traditional breeding, via transformation, or both) to yield a canola plant with superior agronomic performance. If nucleic acids from a plant are positive for a desired genetic marker allele, the plant may be self-fertilized in some embodiments to create a true breeding line with the same genotype, or it may be crossed with a plant comprising the same marker allele, or other desired markers and/or characteristics to create a sexually-crossed hybrid generation.

Often, a method of the present invention is applied to at least one related canola plant such as from progenitor or descendant lines in the subject canola plants pedigree such that inheritance of the desired blackleg resistance allele can be traced. The number of generations separating the canola plants being subject to the methods of the present invention will generally be from 1 to 20, commonly 1 to 5, and typically 1, 2, or 3 generations of separation, and quite often a direct descendant or parent of the canola plant will be subject to the method (i.e., one generation of separation).

Genetic diversity is important in breeding programs. With limited diversity, the genetic gain achieved in a breeding program will eventually plateau when all of the favorable alleles have been fixed within the elite population. Therefore, one objective of plant breeding is to incorporate diversity into an elite pool without losing the genetic gain that has already been made, and with the minimum possible investment. MAS provide an indication of which genomic regions, and which favorable alleles from the original ancestors, have been selected for and conserved over time, facilitating efforts to incorporate favorable variation from exotic germplasm sources (parents that are unrelated to the elite gene pool) in the hopes of finding favorable alleles that do not currently exist in the elite gene pool. Thus, in some embodiments, markers described herein may be used for MAS in crosses involving (elite 33 exotic) canola lines by subjecting segregating progeny to MAS to maintain major yield alleles, along with the blackleg resistance marker alleles herein.

The molecular marker loci and alleles described herein (e.g., DBSNP02349, DBSNP09246, DBSNP01407, DBSNP05863, DBSNP01261, and DBSNP07427, and markers linked to at least one of the foregoing) may be used in some embodiments, as indicated previously, to identify a blackleg resistance QTL, which may then be cloned by familiar procedures. Such increase blackleg resistance clones may be first identified by their genetic linkage to markers described herein. For example, "positional gene cloning" takes advantage of the physical proximity of a blackleg resistance marker to define an isolated chromosomal fragment containing a blackleg resistance QTL gene. The isolated chromosomal fragment may be produced by such well-known methods as, for example and without limitation, digesting chromosomal DNA with one or more restriction enzymes, by amplifying a chromosomal region using PCR, and any suitable alternative amplification reaction. The digested or amplified fragment may subsequently be ligated into a vector suitable for replication and/or expression of the inserted fragment. Markers that are adjacent to an ORF associated with a phenotypic trait may be specifically hybridized to a DNA clone (e.g., a clone from a genomic DNA library), thereby identifying a clone on which the ORF (or a fragment of the ORF) is located. If a marker is more distant from the blackleg resistance QTL gene, a fragment containing the ORF may be identified by successive rounds of screening and isolation of clones, which together comprise a contiguous sequence of DNA. This process is commonly referred to as "chromosome walking," and it may be used to produce a "contig" or "contig map."

Protocols sufficient to guide one of skill through the isolation of clones associated with linked markers are found in, for example, Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989; and Ausubel et al., Eds., *Current Protocols in Molecular Biology*, Chapter 2, Greene Publishing and Wiley-Interscience, NY, 1995.

Plants Comprising Markers for Blackleg Resistance

Some embodiments include methods for making a canola plant, and further include these canola plants, per se. In particular embodiments, such a method may comprise crossing a first parent canola plant comprising at least one marker allele that is positively correlated with blackleg resistance with a second canola plant at a marker linked to blackleg resistance described herein, and growing the female canola plant under plant growth conditions to yield canola plant progeny. Such canola plant progeny may be assayed for marker alleles linked to blackleg resistance, and desired progeny may be selected. Such progeny plants, or seed thereof, may be subject to a variety of uses including, for example and without limitation, they may be sold commercially for canola production; used for food; processed to obtain a desired canola product (e.g., canola oil or canola meal); and/or further utilized in subsequent rounds of breeding. Canola plants according to some embodiments include progeny plants that comprise at least one of the allelic forms of the markers described herein, such that further progeny are capable of inheriting the marker allele.

Some embodiments include methods for producing a canola plant comprising blackleg resistance. In particular embodiments, such methods may include production of such a plant by conventional plant breeding or by introducing an exogenous DNA (e.g., a transgene) into a canola variety or plant.

Thus, some embodiments include host cells and organisms that are transformed with nucleic acids corresponding to a blackleg resistance QTL identified using at least one marker linked to blackleg resistance described herein. In some examples, such nucleic acids may include chromosome intervals (e.g., genomic fragments), ORFs, and/or cDNAs that encode expression products that contribute to a blackleg resistance phenotype.

Host cells may be genetically engineered (e.g., transduced, transfected, transformed, etc.) with a vector (e.g., a cloning vector, shuttle vector, or expression vector) that comprises an ORF linked to a marker of blackleg resistance. Vectors include, for example and without limitation, plasmids; phagemids; *Agrobacterium*; viruses; naked polynucleotides (linear or circular); and conjugated polynucleotides.

Many vectors may be introduced into bacteria, especially for the purpose of propagation and expansion.

Vectors may be introduced into plant tissues, cultured plant cells, and plant protoplasts by any of a variety of standard methods known in the art including, for example and without limitation: electroporation (From et al. (1985) Proc. Natl. Acad. Sci. USA 82:5824); infection by viral vectors such as cauliflower mosaic virus (CaMV) (see, e.g., U.S. Pat. No. 4,407,956); ballistic penetration by small particles comprising the nucleic acid (Klein et al. (1987) Nature 327:70); use of pollen as vector (PCT International Patent Publication No. WO 85/01856); and use of *Agrobacterium tumefaciens* or *A. rhizogenes* carrying a T-DNA plasmid in which DNA fragments are cloned (Fraley et al. (1983) Proc. Natl. Acad. Sci. USA 80:4803). Any suitable method, including without limitation the specific methods explicitly identified herein, which provides for effective introduction of a nucleic acid into a cell or protoplast, may be employed in certain embodiments of the invention.

Engineered host cells can be cultured in conventional nutrient media or media modified for, for example, activating promoters or selecting transformants. In some embodiments, host plant cells may be cultured into transgenic plants. Plant regeneration from cultured protoplasts is described in, for example, Evans et al. (1983) "Protoplast Isolation and Culture," In *Handbook of Plant Cell Cultures* 1, MacMillan Publishing Co., NY, pp. 124-176; Davey (1983) "Recent Developments in the Culture and Regeneration of Plant Protoplasts," In *Protoplasts*, Birkhauser, Basel, pp. 12-29; Dale (1983) "Protoplast Culture and Plant Regeneration of Cereals and Other Recalcitrant Crops," In *Protoplasts*, supra, pp. 31-41; and Binding (1985) "Regeneration of Plants," In *Plant Protoplasts*, CRC Press, Boca Raton, Fla., pp. 21-73. Additional resources providing useful details regarding plant cell culture and regeneration include Payne et al. (1992) *Plant Cell and Tissue Culture in Liquid Systems*, John Wiley & Sons, Inc., NY; Gamborg and Phillips (eds.) (1995) *Plant Cell, Tissue and Organ Culture; Fundamental Methods*, Springer Lab Manual, Springer-Verlag (Berlin Heidelberg N.Y.); and R. R. D. Croy (Ed.) *Plant Molecular Biology* (1993) Bios Scientific Publishers, Oxford, UK (ISBN 0 12 198370 6).

Transformed plant cells that are produced using any of the above transformation techniques may be cultured to regenerate a whole plant that possesses the transformed genotype and thus the desired phenotype. Such regeneration techniques generally rely on manipulation of certain phytohormones in a tissue culture growth medium, typically relying on a biocide and/or herbicide marker that has been introduced into the cell together with the desired nucleotide sequences. Regeneration and growth processes used to produce a whole plant generally include the steps of selection of transformant cells and shoots; rooting the transformant shoots; and growth of the plantlets in soil.

Plant transformation with nucleic acids that provide blackleg resistance (e.g., that comprise markers described herein) may be used to transform species other than canola. For example, it is contemplated that expression products from QTLs that contribute to or provide a blackleg resistance phenotype in canola can also confer blackleg resistance when transformed and expressed in other agronomically and horticulturally important plant species. Such species include dicots, for example and without limitation, of the genera: *Sinapis, Raphanus, Descurainia, Sisymbrium*, and *Thlaspi* in addition to the various members of the Brassicaceae family, including oilseed rape (canola), rutabaga (swede), oilseed turnip rape, turnip, kale, cress, radish, horseradish, stock, bok choy, broccoli, and vegetable and seed crops of cabbage. Common crop plants which may be used in particular examples include, for example and without limitation: canola, broccoli, brussel sprouts, cabbage, cauliflower, kale, and kohlrabi.

Systems for Detecting and/or Correlating Blackleg Resistance Markers

Systems, including automated systems, for identifying plants that comprise at least one marker linked to the blackleg resistance phenotype in canola, and/or for correlating presence of a specific linked marker allele with blackleg resistance, are also included in some embodiments. Exemplary systems may include probes useful for allele detection at a marker locus described herein; a detector for detecting labels on the probes; appropriate fluid handling elements and temperature controllers, for example, that mix probes and templates and/or amplify templates; and/or system instructions that correlate label detection to the presence of a particular marker locus or allele.

In particular embodiments, a system for identifying a canola plant predicted to have blackleg resistance is provided. Such a system may include, for example and without limitation: a set of marker primers and/or probes configured to detect at least one allele of at least one marker linked to blackleg resistance (e.g., DBSNP02349, DBSNP09246, DBSNP01407, DBSNP05863, DBSNP01261, DBSNP07427, and a marker linked to at least one of the foregoing); a detector that is configured to detect one or more signal outputs from the set of marker probes or primers, or amplicon thereof, thereby identifying the presence or absence of the allele; and system instructions that correlate the presence or absence of the allele with blackleg resistance.

A system that performs marker detection and/or correlation may include a detector that is configured to detect one or more signal outputs from the set of marker probes or primers, or amplicon thereof. The precise configuration of the detector may depend on the type of label used to detect a marker allele. Particular examples may include light detectors and/or radioactivity detectors. For example, detection of light emission or other property of a labeled probe may be indicative of the presence or absence of a marker allele interacting with the probe (e.g., via specific hybridization). The detector(s) optionally monitors one or a plurality of signals from an amplification reaction. For example, a detector may monitor optical signals which correspond to "real time" amplification assay results.

A wide variety of signal detection devices are available including, for example and without limitation, photo multiplier tubes; spectrophotometers; CCD arrays; arrays and array scanners; scanning detectors; phototubes and photodiodes; microscope stations; galvo-scanns; and microfluidic nucleic acid amplification detection appliances. In addition to the type of label used to detect a marker allele, the precise configuration of a detector may depend, in part, on the instrumentation that is most conveniently obtained for the user. Detectors that detect fluorescence, phosphorescence, radioactivity, pH, charge, absorbance, luminescence, temperature, or magnetism may be used in some examples.

The precise form of instructions provided in a system according to some embodiments may similarly vary, depending on the components of the system. For example, instructions may be present as system software in one or more integrated unit(s) of the system, or they may be present in one or more computers or computer readable media operably coupled to a detector. In some examples, system instructions include at least one reference table that includes a correlation between the presence or absence of a particular marker allele in a plant or germplasm and the presence or absence of blackleg resistance. Instructions may also include directions for establishing a user interface with the system; e.g., to permit a user to view results of a sample analysis and to input parameters into the system.

A system may include in particular embodiments components for storing or transmitting computer readable data representing or designating detected marker alleles, for example, in an automated (e.g., fully automated) system. For example, a computer readable media may be provided that includes cache, main, and storage memory, and/or other electronic data storage components (e.g., hard drives, floppy drives, and storage drives) for storage of computer code. Data representing alleles detected by the method of the present invention can also be electronically, optically, or magnetically transmitted in a computer data signal embodied in a transmission medium over a network, such as an intranet or internet or combinations thereof. A system may also or alternatively transmit data via wireless, infrared, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

In some embodiments, a system may be comprised of separate elements, or may alternatively be integrated into a single unit for convenient detection of markers alleles, and optionally for additionally performing marker-phenotype correlations. In particular embodiments, the system may also include a sample, for example and without limitation, genomic DNA; amplified genomic DNA; cDNA; amplified cDNA; RNA; and amplified RNA, from canola or from a selected canola plant tissue.

Automated systems provided in some embodiments optionally include components for sample manipulation; e.g., robotic devices. For example, an automated system may include a robotic liquid control armature for transferring solutions (e.g., plant cell extracts) from a source to a destination (e.g., from a microtiter plate to an array substrate) that may be operably linked to a digital computer (e.g., in an integrated computer system). An input device for entering data to the digital computer to control high throughput liquid transfer by the robotic liquid control armature (and, optionally, to control transfer by the armature to the solid support) may also be a feature of an automated system. Many automated robotic fluid handling systems are commercially available. For example, a variety of automated systems that utilize various Zymate™ systems, and typically include, robotics and fluid handling modules, are available from Caliper Technologies Corp. (Hopkinton, Mass.). Similarly, the common ORCA® robot, which is used in a variety of laboratory systems (e.g., for microtiter tray manipulation) is also commercially available from, for example, Beckman Coulter, Inc. (Fullerton, Calif.). As an alternative to conventional robotics, microfluidic systems for performing fluid handling and detection are now widely available from Caliper Technologies and Agilent technologies (Palo Alto, Calif.).

In particular embodiments, a system for molecular marker analysis may include, for example and without limitation, a digital computer comprising high-throughput liquid control software; a digital computer comprising image analysis software for analyzing data from marker labels; a digital computer comprising data interpretation software; a robotic liquid control armature for transferring solutions from a source to a destination; an input device (e.g., a computer keyboard) for entering data into the system (e.g., to control high throughput liquid transfer by the robotic liquid control armature); and an image scanner for digitizing label signals from labeled probes.

Optical images (e.g., hybridization patterns) viewed and/or recorded by a camera or other device (e.g., a photodiode and data storage device) may be further processed in any of the embodiments herein. For example and without limitation, such images may be processed by digitizing the image and/or storing and analyzing the image on a computer. A variety of commercially available peripheral equipment and software is available for digitizing, storing and analyzing a digitized video or digitized optical image, for example, using various computer and programming platforms.

Some embodiments also include kits useful for identifying plants that comprise at least one marker linked to blackleg resistance in canola, and/or for correlating presence of a specific linked marker allele with blackleg resistance. In some examples, such a kit may include appropriate primers or probes for detecting at least one marker linked to blackleg resistance and particular marker alleles; and instructions for using the primers or probes to detect the at least one marker and correlate the marker allele with blackleg resistance. A kit may in some examples include packaging materials for packaging probes, primers, and/or instructions; and controls (e.g., control amplification reactions that include probes, primers or template nucleic acids for amplifications, and molecular size markers).

In some embodiments, a kit or system for identifying plants that comprise at least one marker linked to blackleg resistance in canola, and/or for correlating presence of a specific linked marker allele with blackleg resistance may include nucleic acids that detect particular SSR QTL markers described herein. For example, a system or kit may comprise an amplification primer pair capable of initiating DNA polymerization by a DNA polymerase on a canola nucleic acid template to generate a canola marker amplicon, where the marker amplicon corresponds to a canola marker selected from DBSNP02349, DBSNP09246, DBSNP01407, DBSNP05863, DBSNP01261, and DBSNP07427, and a marker linked to at least one of the foregoing. For example, the primer pair that is specific for the marker can be selected from the primer pairs set forth in Table 3, or their equivalents.

EXAMPLES

The following examples are offered to illustrate, but not to limit, certain embodiments of the invention. It is understood that the examples and embodiments described herein are for illustrative purposes only, and persons skilled in the art will recognize various reagents, techniques, systems, and parameters that can be altered without departing from the spirit or scope of the invention.

Example 1

Plant material and DNA extraction

The Nex845CL/NT152344//Nex845CL population, consisting of 708 BC1F1 progeny, was used for fine mapping Rlm2. Nex845CL, a Dow AgroSciences (DAS) spring canola line with the Omega-9 oil profile, is the recurrent parent. NT152344, a spring canola line, is the Rlm2 donor parent.

DNA was extracted using the MagAttract DNA extraction method (Qiagen, Valencia, Calif.) using the Biocel 1800 (Agilent Technologies, Santa Clara, Calif.). DNA was quantified using the Nanodrop 8000 Spectrophotometer (Thermo Scientific, Rockford, Ill.) per manufacturer's instructions.

Example 2

Phenotyping the Mapping Population

Plant Grow Out

Seeds were sown in soil in a 36-well insert flats in growth chambers. Single plant was inoculated on 4 lobes of the cotyledon. Normal plant growing conditions were maintained (16:8 light/dark photoperiods, 19° C. at day time and 16° C. at night). Watering and fertilization were applied as normal.

Inoculation

Inoculation was done at 10 days after planting when cotyledons were fully expanded. Each lobe of the cotyledon was wounded using a tissue teeth forceps. Ten microliters (µl) of *Leptosphaeria maculans* (*L. maculans*) pycnidiospore suspension in $H_2O$ at a concentration of $2\times10^7$ spores/ml using a repeating pipette was dropped on each lobe. Four droplets on two cotyledons were dropped on a single plant. In cases where a single plant was used from segregating populations, for example backcross or F2 populations, 4 ratings of one plant were treated as replicates. Inoculated cotyledons were kept at room temperature for 6-8 hours before being moved back to growth chambers.

Rating

Disease symptoms were recorded on 10, 12, and 14 days post inoculation (dpi). Symptoms started to appear in 7 dpi as limited necrotic tissue around the wound in resistant phenotypes and as a faint bleaching around wound in susceptible phenotypes. 0-9 rating scales were assigned to each inoculation site at the time of rating according to lesion size, amount of dark margin around the wound, and presence of tissue collapse and sporulation (Table 1).

TABLE 1

Disease rating and description for *L. maculans*.

| Rating | Description |
|---|---|
| 0 | No darkening around wound; the same as water control. |
| 1 | Limited blackening around wound, lesion diameter = 0.5-1.5 mm; faint chlorotic halo may be present; sporulation absent. |
| 3 | Dark necrotic lesions, 1.5-3.0 mm, chlorotic halo may be present; sporulation absent. |
| 5 | 3-6 mm lesion, sharply delimited by dark necrotic margin; may show grey-green tissue collapse as in scales 7 and 9 or dark necrosis throughout; sporulation absent. |
| 7 | Grey-green tissue collapse 3-5 mm diameter; sharply delimited, no darkened margin; sporulation absent. |
| 9 | Rapid tissue collapse, accompanied by profuse sporulation in large, more than 5 mm lesion with diffuse margins. |

Disease Index Calculation and Classification

A disease index (DI) was calculated based on the formula:

$$DI = \frac{\sum_{i=0}^{9} (I \times j)}{n}$$

Where n=total plants, i=rating scales, and j=number of plants/scale. Plants with a DI<3 were classified as resistant; those with a DI=3-5 were classified as intermediate resistant; plants with a DI>5 were scored as susceptible.

Example 3

The KBioscience Competitive Allele-Specific PCR Genotyping System (KASPar™)

The KASPar™ genotyping system is comprised of two components (1) the SNP-specific assay (a combination of three unlabelled primers), and (2) the universal Reaction Mix, supplied at 2× concentration, and containing Taq polymerase enzyme, the passive reference dye, ROX, 50 mM $MgCl_2$, and DMSO. The three primers, allele-specific 1 (A1), allele-specific 2 (A2), and common (C1), or reverse, were designed using the assay design algorithm of the workflow manager, Kraken (KBiosciences, Hoddesdon, Hertfordshire, UK).

An Assay Mix of the 3 primers was made, consisting of 12 micromolar (μM) each of A1 and A2 and 30 μM of C1. The universal Reaction Mix was diluted to 1× and an additional amount of $MgCl_2$ is added so that the final $MgCl_2$ concentration of Reaction Mix at 1× concentration is 1.8 millimolar (mM). DNA was dispensed into 384 well PCR plates at a concentration of 1-5 ng/μl per well and was dried down in the plates in a 65° C. oven for 1 hour and 15 minutes. The Assay Mix and universal Reaction Mix were combined in a 1:54 ratio and 4 μl was dispensed into the DNA plates using a liquid handler robot, so that the final amount of the Assay Mix in the plate was 0.07 μl and the final amount of the diluted Reaction Mix was 3.93 μl. GeneAmp PCR system 9700 machines (Applied Biosystems, Foster City, Calif.) were used for thermocycling with the following conditions: 94° C. for 15 minutes, 20 cycles of 94° C. for 10 seconds, 57° C. for 5 seconds, 72° C. for 10 seconds; 22 cycles of 94° C. for 10 seconds, 57° C. for 20 seconds, 72° C. for 40 seconds. After thermocycling was complete, allele-specific fluorescent intensities were read using a PHERAStar® Spectrofluorometer (BMG LabTech, Cary, N.C.) at room temperature and data was uploaded to the Kraken system for analysis.

KASPar™ uses the fluorophores FAM and VIC for distinguishing genotypes. The passive reference dye ROX is also used to allow normalization of variations in signal caused by differences in well-to-well liquid volume. In Kraken, the FAM and VIC data are plotted on the x- and y-axes, respectively. Genotypes can then be determined according to sample clusters (FIG. 1).

SNP markers and a high-density consensus SNP map developed at DAS were leveraged by selecting 40 SNP markers that were mapped on LG N10 in the consensus map and were polymorphic between the mapping parents, Nex845CL and NT152344. Seventeen of the 40 selected SNP markers were successfully converted to KASPar™ assays, and genotyped on the BC1F1 mapping population. Table 2 provides the list of the 17 SNP markers that were converted into KASPar™ assays and were used for fine mapping Rlm2. Table 3 provides the sequences of the KASPar™ primers for the 4 markers that are most tightly linked to Rlm2.

TABLE 2

Sequences of 17 SNP markers used for fine mapping of Rlm2.

| Marker | GD | SNP | Nex845CL Allele | NT152344 Allele | SEQ ID NO |
|---|---|---|---|---|---|
| DBSNP01088 | 0 | [T/C] | C | T | 1 |
| DBSNP02202 | 11 | [T/C] | T | C | 2 |
| DBSNP00564 | 11 | [T/C] | C | T | 3 |
| DBSNP01174 | 13.9 | [T/C] | T | C | 4 |
| DBSNP06824 | 30.3 | [A/G] | A | G | 5 |
| DBSNP02349 | 35.8 | [T/G] | G | T | 6 |
| DBSNP09246 | 38.1 | [A/G] | A | G | 7 |
| DBSNP01407 | 43.8 | [T/C] | C | T | 8 |
| DBSNP05863 | 44.6 | [T/C] | C | T | 9 |
| DBSNP01261 | 44.8 | [C/G] | G | C | 10 |
| DBSNP07427 | 48.9 | [A/C] | A | C | 11 |
| DBSNP07006 | 52.1 | [T/C] | C | T | 12 |
| DBSNP25978 | 52.1 | [A/G] | A | G | 13 |
| DBSNP25979 | 52.1 | [A/C] | C | A | 14 |
| DBSNP25980 | 52.1 | [T/G] | T | G | 15 |
| DBSNP00525 | 52.1 | [A/G] | A | G | 16 |
| DBSNP06060 | 52.3 | [A/C] | C | A | 17 |

GD: Genetic distance;
Nex845CL: Rlm2 susceptible parent;
NT152344: Rlm2 resistant parent.

TABLE 3

Primer sequences of four SNP markers tightly linked to Rlm2. KASPar ™ assays were developed for the four SNP markers.

| Marker | Primer | SEQ ID NO |
|---|---|---|
| DBSNP09246 | Allele Specific Primer 1 | 18 |
|  | Allele Specific Primer 2 | 19 |
|  | Common Reverse Primer | 20 |
| DBSNP01407 | Allele Specific Primer 1 | 21 |
|  | Allele Specific Primer 2 | 22 |
|  | Common Reverse Primer | 23 |
| DBSNP05863 | Allele Specific Primer 1 | 24 |
|  | Allele Specific Primer 2 | 25 |
|  | Common Reverse Primer | 26 |
| DBSNP01261 | Allele Specific Primer 1 | 27 |
|  | Allele Specific Primer 2 | 28 |
|  | Common Reverse Primer | 29 |

Example 4

Linkage analysis and map construction

MAPMAKER/EXP 3.0 (Lander et al. 1987) was used to construct a linkage group (LG) at LOD score 10.0 to confirm that the markers were mapped with their phenotypic trait together on LG N10. MAPMAKER/EXP 3.0 requires only one input file from each population, referred to as a locus genotype file. In the locus genotype file of the population, elite parent alleles were called "A", donor parent alleles were called "B", while heterozygous alleles were called "H". Missing data were represented with a dash (-) in the locus genotype file.

A genetic linkage map of LG N10 with 17 SNP markers was constructed. Since Rlm2 is a qualitative, single race-specific trait, the phenotypic data was classified as R (DI<5) and S (DI>5), and mapped as a marker on the LG N10 linkage map. Four SNP markers DBSNP09246, DBSNP01407, DBSNP05863 and DBSNP01261 within 2.6-3.6 cM to blackleg resistance Rlm2 were identified (FIG. 2). The two closest markers flanking SNP markers DBSNP01407 and DBSNP09246 were, respectively, 2.6 cM and 3.1 cM to Rlm2 (FIG. 2). The four high throughput SNP markers identified and developed at DAS greatly facilitate the marker assisted selection of Rlm2 n the DAS breeding program.

What may be claimed is:

1. A method of introgressing at least one blackleg resistance QTL into a canola plant, said method comprising
   a. crossing a blackleg resistant canola plant with a second canola plant to form a population;
   b. screening said population with at least one nucleic acid marker selected from the group consisting of DBSNP 02349, DBSNP 09246, DBSNP 01407, DBSNP 05863, DBSNP 01261, and DBSNP 07427; and
   c. selecting from said population one or more canola plants comprising at least one genotype corresponding to the blackleg resistant canola plant.

* * * * *

```
                         SEQUENCE LISTING

<160> NUMBER OF SEQ ID NOS: 29

<210> SEQ ID NO 1
<211> LENGTH: 1652
<212> TYPE: DNA
<213> ORGANISM: Brassica napus
<220> FEATURE:
<221> NAME/KEY: misc_feature
<222> LOCATION: (259)..(259)
<223> OTHER INFORMATION: n is a, t, c, or g
<220> FEATURE:
<221> NAME/KEY: misc_feature
<222> LOCATION: (283)..(283)
<223> OTHER INFORMATION: n is a, t, c, or g
<220> FEATURE:
<221> NAME/KEY: misc_feature
<222> LOCATION: (569)..(569)
<223> OTHER INFORMATION: n is a, t, c, or g
<220> FEATURE:
<221> NAME/KEY: misc_feature
<222> LOCATION: (597)..(597)
<223> OTHER INFORMATION: n is a, t, c, or g
<220> FEATURE:
<221> NAME/KEY: misc_feature
<222> LOCATION: (618)..(618)
<223> OTHER INFORMATION: n is a, t, c, or g
<220> FEATURE:
<221> NAME/KEY: misc_feature
<222> LOCATION: (640)..(640)
<223> OTHER INFORMATION: n is a, t, c, or g
<220> FEATURE:
<221> NAME/KEY: misc_feature
<222> LOCATION: (656)..(656)
<223> OTHER INFORMATION: n is a, t, c, or g
<220> FEATURE:
<221> NAME/KEY: misc_feature
<222> LOCATION: (674)..(674)
<223> OTHER INFORMATION: n is a, t, c, or g
<220> FEATURE:
<221> NAME/KEY: misc_feature
<222> LOCATION: (694)..(694)
<223> OTHER INFORMATION: n is a, t, c, or g
<220> FEATURE:
<221> NAME/KEY: misc_feature
<222> LOCATION: (746)..(746)
<223> OTHER INFORMATION: n is a, t, c, or g
<220> FEATURE:
<221> NAME/KEY: misc_feature
<222> LOCATION: (790)..(790)
<223> OTHER INFORMATION: n is a, t, c, or g
<220> FEATURE:
<221> NAME/KEY: misc_feature
<222> LOCATION: (821)..(821)
<223> OTHER INFORMATION: n is a, t, c, or g
<220> FEATURE:
<221> NAME/KEY: misc_feature
<222> LOCATION: (821)..(821)
<223> OTHER INFORMATION: n is a, t, c, or g
<220> FEATURE:
<221> NAME/KEY: misc_feature
<222> LOCATION: (829)..(829)
<223> OTHER INFORMATION: n is a, t, c, or g
<220> FEATURE:
<221> NAME/KEY: misc_feature
<222> LOCATION: (850)..(850)
<223> OTHER INFORMATION: n is a, t, c, or g
<220> FEATURE:
<221> NAME/KEY: misc_feature
<222> LOCATION: (876)..(876)
<223> OTHER INFORMATION: n is a, t, c, or g
<220> FEATURE:
<221> NAME/KEY: misc_feature
<222> LOCATION: (914)..(914)
```

<223> OTHER INFORMATION: n is a, t, c, or g

<400> SEQUENCE: 1

```
gaggaccggt cggaattccc gggtcgaccc acgcgtccgt ttttctcttc caccccacaa      60
agttaaccgg aagaggaaaa taaaataaaa actaaagaaa tgattctcca caaaatggcg     120
ttcttggccg ctattctttt cttctttgta agcagcagca ttcacgttca cagccgcgaa     180
acgtttgctt gcgatacaaa ggacgcagca acagcgacgc tgagattctg tcagcagtca     240
gttccgatac cggagagang taaaggattt gatcggacgg ctngacgttg gccgagaaag     300
taagcttgtt aggaaacact gcggcggcga ttccacggct aggaattaaa gggtacgagt     360
ggtggtcgga ggctttacac ggcgtttcaa atgtgggtcc cggtacyaag ttcgctgggc     420
ccttccctgc ggccaccagt ttccctcaag tcatcaccac tgctgcttcc ttcaatgcct     480
ccttgtggga atccatcgga cgggttgtgt caaatgaggc cagggccatg tataacggtg     540
gagttggtgg gcttacatac tggagcccna acgttaaca tattgcggga cccgcgnttg      600
gggacgtgga caggaaanct cccggtgaag accctgtccn tagctggtaa atacgnccgc     660
cagctacgta aganggttta cagggaaacg accngtagcc ggttgaaagt cgccgcctgt     720
tgcaaacatt tcacggcgta cgatcntcga caactggaac ggcgtcgata gattccattt     780
caacgctaan ggtgagcaag caagacatag aagacacgtt ncgatgttnc ctttccgtat     840
gtgtgtgaan ggaaggaaac gtggcgagca ttatgntgtt cgtacaatca agttaatggc     900
gttccgacat gtgnccgatc ctaacctcct gaaaagacc atacgtaacc aatggggtct     960
caacggatac atcgtctccg actgtgactc tgttggtgtt ctatacgata cacaacatta    1020
cactggtact cctgaagaag cagccgctaa atccatcaaa gctggcttgg atttggattg    1080
tggaccgttc ctaggagctc ataccatcga cgccgtgaac aaaaacctgt tgcgtgagtc    1140
agacgttgac aatgccgtag tcaacacgct aacagtacaa atgagactag aatgttcga    1200
cggcgatata gcgactcagc cttacggaca ccttggatca gcacatgttt gtacaccggt    1260
tcacaaggga ctagctctcg aagcagctca tcaaggaatc gtcctcctca gaacctcgg    1320
cccgtctcta cctctctctc gtcaccgcca ccgtacggtc gctgttatcg gaccaaatgc    1380
ggacgcaaca gtcacaatga ttggtaacta cgcaggtatt gcttgtggat ataccagtcc    1440
ggttcaagga atagccggtt atgcacgaac cgttcacaac aagggttgcg cggacgtgca    1500
ctgcatggac gatagattgt tcgatggtgc ggctgacgca gctcgtggat ctgatgcgac    1560
ggttctcgtg atgggtttgg accagtctat tgaagctgag ttcaaggaca gaaacagttt    1620
gcttttgcct ggaaaacaac aagagcttat ct                                  1652
```

<210> SEQ ID NO 2
<211> LENGTH: 1498
<212> TYPE: DNA
<213> ORGANISM: Brassica napus
<220> FEATURE:
<221> NAME/KEY: misc_feature
<222> LOCATION: (90)..(90)
<223> OTHER INFORMATION: n is a, t, c, or g
<220> FEATURE:
<221> NAME/KEY: misc_feature
<222> LOCATION: (365)..(365)
<223> OTHER INFORMATION: n is a, t, c, or g
<220> FEATURE:
<221> NAME/KEY: misc_feature
<222> LOCATION: (490)..(490)
<223> OTHER INFORMATION: n is a, t, c, or g
<220> FEATURE:
<221> NAME/KEY: misc_feature

```
<222> LOCATION: (495)..(495)
<223> OTHER INFORMATION: n is a, t, c, or g
<220> FEATURE:
<221> NAME/KEY: misc_feature
<222> LOCATION: (505)..(505)
<223> OTHER INFORMATION: n is a, t, c, or g
<220> FEATURE:
<221> NAME/KEY: misc_feature
<222> LOCATION: (575)..(575)
<223> OTHER INFORMATION: n is a, t, c, or g
<220> FEATURE:
<221> NAME/KEY: misc_feature
<222> LOCATION: (635)..(635)
<223> OTHER INFORMATION: n is a, t, c, or g
<220> FEATURE:
<221> NAME/KEY: misc_feature
<222> LOCATION: (770)..(770)
<223> OTHER INFORMATION: n is a, t, c, or g
<220> FEATURE:
<221> NAME/KEY: misc_feature
<222> LOCATION: (1087)..(1087)
<223> OTHER INFORMATION: n is a, t, c, or g
<220> FEATURE:
<221> NAME/KEY: misc_feature
<222> LOCATION: (1133)..(1133)
<223> OTHER INFORMATION: n is a, t, c, or g
<220> FEATURE:
<221> NAME/KEY: misc_feature
<222> LOCATION: (1478)..(1478)
<223> OTHER INFORMATION: n is a, t, c, or g
<220> FEATURE:
<221> NAME/KEY: misc_feature
<222> LOCATION: (1481)..(1481)
<223> OTHER INFORMATION: n is a, t, c, or g
<220> FEATURE:
<221> NAME/KEY: misc_feature
<222> LOCATION: (1489)..(1489)
<223> OTHER INFORMATION: n is a, t, c, or g

<400> SEQUENCE: 2
cgggtcgacg atttcgtttc accgagattt tattccttt tcgcattagc gacaaatccc      60 cctttctag gtcgtcacga tgcagcagcn caccacaaaa cgccgccgga gcagggcagc    120
agatcccttc tgaccagcaa gcctatcacc agcagcaact ctcgtggatg atgcaacagc   180
aacagggcca gcaatggaac cagcagtcag cgccgtcaca gggtcaacag ccctacggat   240
ctcagaatcc aggatccgat aacgagattc gctccytgtg gatcggcgcc ttgcagccgt   300
ggatggacga aagctacatc atgaccgtct tcgctcaggc cggcgaggtt caatcggcta   360
aagtngattc gcaataaact gactggtatg tgcgagggtt acggattcgt tgagttcgct   420
aaccacgctg cagctgagcg tgtgttgcag acctacaacg gtactcagat gcctaactct   480
gaccagaccn tttanggctg aactngggct caggccgggg ctggtgagag cgccaagct    540 gaagggcctg agtacactat ctttgtgggc gaccntggct cctgaagtta ctgacttcat   600
gctcgcggag acgttttcga atgtgtacgc gtctngtcaa gggggctaag gttatgatgg   660
acaggagcac tggacggacg aagggatatg ggtttgttag gtttgggat gaaagtgagc   720 agatgcgtgc gatggggaa atgaatggtc agtactgctc gagtaggccn tatgcgtctt   780
ggtcccgctg ccaacaagaa gccgcttgca atgcagccag gcatgtatca ggacacccaa   840
ggaggaggaa atcctggaga aagcgatcca agtaacacaa ctatatttgt tggtgctctg   900
gatgctagcg ttacagacga agaattgagg gcagttttg gtcaattggg agaacttact    960
cacgtgaaaa tacctccggg gaagcgttgt ggattcgttc agtatgccac cagggcgtct  1020
gcggagcatg cacttttaaa tctgaatgga acacaattag gtggacaaag catccgtctt  1080
tcatggngga cgtagtccga acaaccaggc acagcctcat caagctcaat ggnaatggtg  1140
```

```
gtggtggata ctatggatac cctccacagc cgcagggctt tgaaccatat ggtcatggag   1200
ctcctcgtcc tcaggatcct agtgcgtact atggtggcgg ttacggtggc tatggcaact   1260
atcagcagca acggcagtga aagatcaaca acaccagctt tttctaccaa agtcttggac   1320
aatgggcaaa atatatatca gtcatcgttg agtcttgata ggaaattaga tttaaaagtg   1380
ttttgtcttt tacatgaagt gagtatggtt ttgctattgg gttaatgttg tgttcttaaa   1440
ccaaaaaaat aataaggttg gatttgctat ggacatgntt natgtaatnt tgaaactc    1498
```

\<210\> SEQ ID NO 3
\<211\> LENGTH: 886
\<212\> TYPE: DNA
\<213\> ORGANISM: Brassica napus
\<220\> FEATURE:
\<221\> NAME/KEY: misc_feature
\<222\> LOCATION: (805)..(805)
\<223\> OTHER INFORMATION: n is a, t, c, or g

\<400\> SEQUENCE: 3

```
cacgcgtccg ctctgcgcaa caatggctct cttcgttcta tctctcctaa tgctctcatc     60
attctcagcc atttccttca cgcatgcaga ttctggaatg atcggagtaa actacggccg    120
catagcgaac aatctcccgg cgccggagaa ggtcgttgag cttctaaaat cccaaggaat    180
caatcgcgtc aagctttacg acactgacaa atccgtacta accgcgctcg caaactccgg    240
catcaaagtc gtcgtctctc tcccaacga  gaatctcgcc gccgcctccg ctgatcagag    300
ctacaccgac aactgggttc aggaaaacgt gaagaaatac acgccggcga ctgatatcga    360
agcgatcgcc gtcggtaacg aagtgttcgt tgatcctaga aacacgacga cgtatctcgt    420
tcaagctatg aagaatgttc agagctcgct cgttaagttt aatctcgacg aatcgattaa    480
ggtatcgtcg ccgattgcct tgagcgcgyt ggcgaattcg tatccaccat cgtccggttc    540
gtttaaaccg gatttaatcg aaccggtgat taaaccgatg ttggatctgc tccgcaaaac    600
gtcgtcgcat ataatggtga atgcgtaccc gttcttcgcc tacgcggcta acgccgataa    660
gatctcgttg gattacgctc tgtttaagga gaactccgga aatgtagatt ccggtaacgg    720
tttgaagtat aacaatctct tagacgcgca aatcgacgcc gttttcgccg ccatggccgc    780
cgtgggattc aacgacgtta agctncgtgg tgacggagac gggttggcct tccgccgggg    840
acgagaacga gattggcgcc ggttcggcca acgcggcggc gtataa                   886
```

\<210\> SEQ ID NO 4
\<211\> LENGTH: 1509
\<212\> TYPE: DNA
\<213\> ORGANISM: Brassica napus

\<400\> SEQUENCE: 4

```
tcgacgattt cgttcatctg cttgtgcgcg ggaataagaa ttcatagccg gaaatggcga     60
aagacgacgt ggagatgcga ggggaggccg aggagcgcat aatcaacgaa gactacaaga    120
tctggaagaa gaacactcct ttcctctacg acctcgtcat cactcacgct ctcgagtggc    180
cttcccttac cgttgaatgg ctccccagcc gcgatgagcc tcccggtcaa aactactccg    240
tccagaagat gcttctcggt acccacactt ccgayaacga acccaattat ctcatgattg    300
cccaggttca gcttccccttg aagacaccg  aaagcgaagc gcgtcaatac gacgacgatc    360
gctccgagtt tggtgggttt ggctgcgcct ccggaaaggt gcaagtgatc cagcagatag    420
ttcacgaagg tgaggtgaac cgagctcgat acatgcctca gaaccctttc ttgattgcca    480
ccaagacggt tagtgcggag gtgtttctgt tcgattacag caagcaccca tctaagccag    540
```

```
cgcttgatgg agcttgcaat cctgatatga agctcaaggg tcacagctct gaaggctatg      600
ggctgtcttg gagtagcttg aaggaaggtc atttgctcag cggcgctgat gacgctcaga      660
tctgcttgtg ggatgttagc gccactcctc aaagcaatgt tcttgacgct cagcagatct      720
tcaaggctca tgaaggcgtc gtggaagatg ttgcatggca tatgagtcat gaacacctgt      780
ttggatccgt tggagatgat cagtaccttc ttatatggga tctgcgttct ccatctgcca      840
gtaagccaat acagtctgtg gttgctcact ccatggaggt taactgttta gccttcaatc      900
caatcaatga gtgggttgtg caacagggt caactgataa gaccgttaaa ttattcgatc       960
tgcggaagct aaccagcgct cttcacacat ttgatagcca taagaggag ttttccaag       1020 ttggatggaa cccgaagaac gagactatct tagcctcatg ttgccttggt agaaggctta     1080
tggtttggga ccttagcagg atcgacgagg agcagacagc agaggatgca gaggacggtc     1140
caccagagct gctgttcatc catggtggcc acaccagcaa aatatcagat tctcatgga     1200 acccatgtga agattgggtt atttccagtg tggctgagga caacatactc agatatggc     1260 aaatggctga gaacatttat catgacgagg atgatgctcc aggggaagaa ccaataaaag    1320
gttcttagct ttaatgttag ctccctatc ttatgtgaca ttaatttct tttacttatc      1380 tctctgcctt tgatctgttc atctgttcaa gtatttagtg taagttatgt aaaacgagac    1440
atgaaatgag tttaccctt tttcttcaaa aaaaaaaaa aaaaactcga ggggggcccg     1500
gtcccatcg                                                              1509

<210> SEQ ID NO 5
<211> LENGTH: 676
<212> TYPE: DNA
<213> ORGANISM: Brassica napus

<400> SEQUENCE: 5
ttctcgcctc cgttttcgct tatccgatct gcgaagatgt tctctgctca gaacaagatc       60
aagaaggaca araatgctgc tacaacggag tgcgatgagc tagttgctca ggctctgttt     120
gatttggaga acaccaacca ggagttgaag agtgacttga agatctcta catcaaccaa      180 gctgttaaca tggacatcgc tggaaaccgc aaggctgttg tgatctacgt cccattcaga     240
ctaaggaaag cttttccgcaa gattcatccc cgtctcgtta gagagcttga gaagaagttt    300
agtggaaagg atgtgatctt tgttgccaca aggaggatca tgcgtccacc caagaagggt    360
gctgctgtcc agaggccacg caacaggact cttacctctg ttcatgaggc tatgctcgag    420
gatgttgctt accctgctga gattgttggt aaacgtactc gttaccgtct tgatggttcc    480
aagatcatga aggtctactt ggataccaag gaaggaaca acacagagta caagctggag    540
actatgattg gtgtgtaccg taaacttact ggaaaggatg tcactttga gtaccctgtc    600 gaagcttgaa aggaagatgc tgaaagaatc acaaggatac tgttttgtgt tatttaggat    660
tatgaaggaa actctt                                                     676

<210> SEQ ID NO 6
<211> LENGTH: 1117
<212> TYPE: DNA
<213> ORGANISM: Brassica napus
<220> FEATURE:
<221> NAME/KEY: misc_feature
<222> LOCATION: (890)..(890)
<223> OTHER INFORMATION: n is a, t, c, or g
<220> FEATURE:
<221> NAME/KEY: misc_feature
<222> LOCATION: (906)..(906)
```

<223> OTHER INFORMATION: n is a, t, c, or g
<220> FEATURE:
<221> NAME/KEY: misc_feature
<222> LOCATION: (943)..(943)
<223> OTHER INFORMATION: n is a, t, c, or g
<220> FEATURE:
<221> NAME/KEY: misc_feature
<222> LOCATION: (1011)..(1011)
<223> OTHER INFORMATION: n is a, t, c, or g
<220> FEATURE:
<221> NAME/KEY: misc_feature
<222> LOCATION: (1026)..(1026)
<223> OTHER INFORMATION: n is a, t, c, or g

<400> SEQUENCE: 6

| | | | | | |
|---|---|---|---|---|---|
| tgttcgcaag | gttcaggtct | ctgctaaatg | tttgactgca | ttgcatccgg | attgtcttca | 60 |
| gctatgtctc | caggccaaga | gctataaagc | tggtttctcc | gttcttagtg | acgatatctt | 120 |
| ggaggttgac | cagcctagag | atttttatct | ctattgctat | tatgggggaa | tgatatgcat | 180 |
| tgggctgaag | agattccaga | aggcatcgga | gcttctttac | aatgttgtta | ctgctccaat | 240 |
| gtatcaactc | aacgccatag | ctcttgaggc | gtacaaaaag | tacatattgg | ttaatctcat | 300 |
| tcactctggc | cagtttagta | acagtgtccc | caagtgcgct | tctacagcag | ctcagaggca | 360 |
| cctaaagagc | tggtgtatac | cttacaacga | agtgggtaat | tgttacaacg | atggggagat | 420 |
| cagtgaacta | gaggcagtgg | ttgtggccca | cagctcagat | tttgaaatgg | acaataacct | 480 |
| tggattagtk | aagcaagcag | tggcatccct | ttacaagcgg | aacattctga | gactcactca | 540 |
| gaagtacgtg | accttgtcgc | ttcaagatat | agccaacatg | gtccaacttg | ctaatgctaa | 600 |
| ggaggcggaa | atgcatgtgc | ttcagatgat | ccatgatggt | cagatacatg | cccttatcaa | 660 |
| ccagaaagat | ggaatggtga | gattcttgga | ggaccctgag | cagtacaaaa | ccagtgagat | 720 |
| gatagaggtc | atggattctg | tcatccaaag | ggctattggg | ctgtcgaaga | atctcatagc | 780 |
| catggatgag | agcttgtcat | gtgatccttt | gtacttggga | aaggttggaa | gggaaaggca | 840 |
| aaagttcgac | ttcggagacg | atattgatac | cgtccctcaa | aagttctccn | atgtaaacag | 900 |
| caaaangacc | tggtggaaca | aaactttaac | tcaaagacaa | ctncctagttg | tgggaatctg | 960 |
| gacaactttc | tttgttcttt | ttttgctggt | ttatgaagtt | tcatatattg | nttttcgcaa | 1020 |
| tagccnaact | agtagagaag | agcgaatcct | aatcattact | taaaaagttt | ctgttagtgt | 1080 |
| cgtctcttgc | ttaattattt | aaagaaaaaa | taagccc | | | 1117 |

<210> SEQ ID NO 7
<211> LENGTH: 367
<212> TYPE: DNA
<213> ORGANISM: Brassica napus

<400> SEQUENCE: 7

| | | | | | |
|---|---|---|---|---|---|
| ctgcagggag | aacatggaat | ctaaatttta | gtgaaattga | atggtggaga | aaaccgaaga | 60 |
| ctgaaccgga | aattgagaaa | gagagaaagt | tgtaccggag | gagaggaaga | gagacgatat | 120 |
| tcrtgcatga | tccaatcggt | tcttgagcca | tgaggtggtt | tgcctttgta | gaaaacgagt | 180 |
| gttttcttca | aaccaacgat | ttgatttcct | cgagaggtca | caacccgttt | atcaataccg | 240 |
| gtagctttcc | aataacccga | accggttgct | cggttagacc | ggttcccatt | tgggtacttg | 300 |
| gcttcccttg | tgctgaagaa | gtacctctcc | ttctccaaat | tgcctggcag | aaatagagag | 360 |
| agtttaa | | | | | | 367 |

<210> SEQ ID NO 8
<211> LENGTH: 694

```
<212> TYPE: DNA
<213> ORGANISM: Brassica napus
<220> FEATURE:
<221> NAME/KEY: misc_feature
<222> LOCATION: (600)..(600)
<223> OTHER INFORMATION: n is a, t, c, or g
<220> FEATURE:
<221> NAME/KEY: misc_feature
<222> LOCATION: (611)..(611)
<223> OTHER INFORMATION: n is a, t, c, or g
<220> FEATURE:
<221> NAME/KEY: misc_feature
<222> LOCATION: (625)..(625)
<223> OTHER INFORMATION: n is a, t, c, or g

<400> SEQUENCE: 8
gatgaaagcg atcatcgttg gaggaagtat agctggcgta tcgtgcgcac actcgctcac        60
gttagcaggc tgggatgtac tagtactcga gaaatcttcc gaacctccgg ctcggagccc       120
tactggtgcg ggactcggac tcgaccctca agctcgcaca atcatcaaat catggcttcc       180
tcatccacac tcttagacg aaaccacctt gcctctctcc atcgatcaga atcaagcaac        240
agatagtgag aagaaagtga ggcgagttct aacgagagac gagagttttg attttcgagc       300
agcttattgg tcagacattc acggtcttct gtttaacgca ttggatccga ccatgtttct       360
ttggggacat aagtttctgt ctttcgctat gtcacaagat ggttccactg taaaggtgga       420
gactttagtt atgaaactc aagagactgt tgagattcaa ggagacttgc tcgttgcagc        480
agatgggtgt ctctcttcya ttcggaaaac gttcttgccg aactttaaac taaggtactc       540
tggttattgc gcttggagag gtgttttttga tttctcaggg gatgagaact cggagacagn      600
tttctggaat ncaagaggga gtatnccaga gcttgggaga tgcttgtatt tcgatcttgc       660
tatgaatact catagcgtgt tctatgagct tatt                                   694

<210> SEQ ID NO 9
<211> LENGTH: 1239
<212> TYPE: DNA
<213> ORGANISM: Brassica napus

<400> SEQUENCE: 9
tttatcctca aaacctaccc tctctccccg ttgtccgaga actcctctgc gtatcctcta        60
gatctgttcg ttttcgaaca tctgttattg cttaatctga gatctaccga tctccgtaca       120
ggttttgttg tccgtatgct gtgttattat cagatctgtg attcctatgg cggagactct       180
caaagaagat tcgataatga ttcgagaggt ctggaacaac aacytcctcg aggaattcgc       240
gctgatccgc gagatcgtcg acaagtaccc cttcatcgcc atggacaccg agttccccgg       300
cgtggtcctc aaacccgtgg aaacgttcaa gtataacaac gatctcaact accgcaccct       360
caaagaaaac gtgatctcc taaaattgat ccagctcggt ctaaccttct ccgacgagga       420
cggcaacctc cccacctgcg gcaccgacaa gttctgcatc tggcagttca acttccgcga       480
gtttaacata ggcgaagaca tctacgctag cgagtccatc gagctgctgc gccagtgcgg       540
gatcgatttc aagaagaacg tcgagaaggg gatcgacgtg gtccggttcg gggagctgat       600
gatgtcctcg gggatcgtgt tgaacgattc gatctcgtgg attactttc atggcggtta       660 tgattttggt tatttggtga agcttctgac ttgcaaggag ctgcctctca ggcaggcgga       720 ttcttcaag atgttgtttg tgtatttccc cacggtttac gatattaagt acttgatgac        780
tttctgcaac gggcttttcg gagggctgaa caggcttgcg gagcttatgg gtgtggagag       840
agttgggatt tgtcatcagg ctgggtcgga tagcttgctc acgttaggct cgtttaggaa       900
```

```
gctcaaggaa cgttatttcc ctgggtcgac tgataagtac actggagtct tgtatggtct      960
aggtgtggaa gattctgcta ctagtactgc tattgctaat taagtttaag aggggatttg     1020
cattaggttt tttcagtctt tgtgagtgtg agaccaatta gactttgtgt ttgtgtaaat     1080
tggttttagt aagtgattgt tgtttctttg tttttttttt cttttcggga aagaaaaaac     1140
ctctttgatc aaatgagcag gggttcttgt aaatgttgca gctttgagct tctgaatgtc     1200
taccatattg caaccccgc ctcattatca aaatcgctc                             1239
```

```
<210> SEQ ID NO 10
<211> LENGTH: 1544
<212> TYPE: DNA
<213> ORGANISM: Brassica napus
<220> FEATURE:
<221> NAME/KEY: misc_feature
<222> LOCATION: (269)..(269)
<223> OTHER INFORMATION: n is a, t, c, or g
<220> FEATURE:
<221> NAME/KEY: misc_feature
<222> LOCATION: (707)..(707)
<223> OTHER INFORMATION: n is a, t, c, or g
<220> FEATURE:
<221> NAME/KEY: misc_feature
<222> LOCATION: (757)..(757)
<223> OTHER INFORMATION: n is a, t, c, or g
<220> FEATURE:
<221> NAME/KEY: misc_feature
<222> LOCATION: (810)..(810)
<223> OTHER INFORMATION: n is a, t, c, or g
<220> FEATURE:
<221> NAME/KEY: misc_feature
<222> LOCATION: (821)..(821)
<223> OTHER INFORMATION: n is a, t, c, or g
<220> FEATURE:
<221> NAME/KEY: misc_feature
<222> LOCATION: (1346)..(1346)
<223> OTHER INFORMATION: n is a, t, c, or g

<400> SEQUENCE: 10
gacttccggg atggagaaga agagagcaaa aatgagcttt aataggatga atatcataat       60
aatcctttgt gtatgtctca actgggactg tagcgaggga gctcaagaaa aacagaggag      120
ggcgattgat tctcatacta tccaactcag ctctctcttc ccttcatcgt catcaccttg      180
tgttcttcct acaagagctt ccagtacaaa gtcctcactg cacgtgacgc acagacacgg      240
cacgtgctcg cgtataacca atgcaaaang ccaagaatcc agaccatgcc gagattctta      300
gactggacca agcgcgcgtc aactcgatac attcgaaact atcgaagaag ctcacagatc      360
gagtcaggca aagcaagtca acggatctac ctgctaaaga cggaagcacc tacggttcag      420
gaaacttcgt cgtaaccctc ggaatcggaa caccgaaaca cgatctgtct ctgatcttcg      480
acacaggaag cgacctgacg tggattcaat gcgagccatg tgttcgaact tgctattccc      540
aaaaggaacc aatctttaac ccgtcctcct cttcctcata ccacaacgts tcttgctcat      600
cggctgagtg tagctcactc tcttccgcta caggtaattc cggaacatgc tcggcttcga      660
actgcgtcta cggtattcaa tacgcgatc aatcgttctc cgttggnttt tctcgccaag      720
gagaagttta cactaacggc gtctaatgtg tttgacnggc gttaacttcg gctgcggcga      780
aaacaaccaa ggactttcta ccggagtcgn ccggacttct ncggcctcgg ccgtgacaag      840
ctctctttcc cgtcgcagac ggcggcgacc tacaacaaga tcttctccta ctgcctccct      900
tcctccgcta gctacaccgg acacctcacc ttcggatccg ccggagtctc cagatccgtt      960
aagttcactc cgatctccac catcaccgac ggcacatcct tctacggtct cgacatcgtc     1020
ggaatctccg tcggcggtca gaaactcgcg attcctccga cggtgttctc cactccggga     1080
```

```
gctctgatcg attccggaac cgtcatctct cgcctcccgc cgaaggccta cgcggcgctg      1140
cgaggcgcgt tcaaggcgaa gatgtcgcag tacaagaata cgtcgggagt ctcgatcttg      1200
gacacgtgtt ttgatctcac cgggttaaaa acggtgacga tcccgacggt gtcgttttac     1260
ttcaatggtg gtgccgtggt gcagcttggc tcgaaagggg ttttgtacgc gtttaagatg      1320
tcgcaggttt gtttggcgtt tgcggngaac agcgatgata ataacgctgc catctttggg     1380
aacgttcagc agcaaacgct ggaagttgtg tacgatggtg cggccgggcg ggtcgggttt      1440
gctccgaatg ggtgtagtta atgaaaacat atgggtaaat tttatttgtg gatttggcgc     1500
caaaatagct ttatccttaa tcaagtgtat aatttgtatg agga                      1544
```

<210> SEQ ID NO 11
<211> LENGTH: 1034
<212> TYPE: DNA
<213> ORGANISM: Brassica napus

<400> SEQUENCE: 11

```
ccaacaacaa caatggcagc cacaagagtg ctcactgcag ctgcagccac tacccaaccc      60
acctcctgtt tcctctccaa acgagctttc cttctcccgg ccaagacatc atccttcgct     120
ctatccttca acagaagagc tttggtgttg aaatcgaagc gamccttctc ttgcagcgcc     180
atttacaacc ctcaaaccaa ggttcaagaa gaaggtcaat ccgaaacctt agattatcgt      240
gtcttcttcc tcgatggtgg ctccggaaag aaggtttctc catggcatga tataccgttg      300
accttaggag atggagtttt caacttcata gttgagatcc ccaaagagtc caaagcaaag      360
atggaggttg ctactgatga agactacact cctattaagc aagacactaa gaagggcaag      420
ctcagatact atccgtacaa cataaactgg aactatggat tgcttccaca gacatgggaa      480
gatccatctc aggctaaccc tgaagttgaa ggagcttttg gtgataatga tccagttgat      540
gttgttgaga ttggggaagc ccaaaggaag ataggagagg ttctaaagat caagcctttg      600
gctgctttag ctatgattga tgaaggggag ctggactgga gattgttgc catttctttg       660 gatgaccctaa agctcatttt tgtgaatgat gttgatgatg ttgagaagca tttccctggt    720
acattgacag ctattagaga ttggtttagg gactacaaga tcccagatgg aaagcctgct     780
aacaggtttg gtcttggaga caaaccagca aacaaagact atgctttgaa gatcatccat     840
gaaacaaatg aatcatgggc taagcttgtg aagagatcag ttgatgctgg agacctttca      900
ctattctgaa cagcttaaga aaattatatc tttgcaatgt cctgtcgtga gctcgaataa     960
tttgattttg atcagtctca tgagtcctac atcattcttg tttctctctt tctaaagaga    1020
gatgtaaaca ttga                                                       1034
```

<210> SEQ ID NO 12
<211> LENGTH: 763
<212> TYPE: DNA
<213> ORGANISM: Brassica napus

<400> SEQUENCE: 12

```
aagcacaacc ctagaaactc gagtcatgag gggtctgatc tccggcgcga agaggctatg       60
gacaacacca ccaccgacgg cgatagccac cgccatagcg agaagaagct acagcgtaat      120
accgatggtt atcgagactt catcgcgagg cgagagagct acgatatct tctcgcgact       180 gctcaaggag cgcataatct gcatcaacgg ccccataaac gacgcacgt cacacgtcgt      240 cgtggctcag cttctctacc tcgagtccga gaatccttcg aagccgattc ayatgtacct      300
```

```
caattcacca ggcggacacg tcaccgccgg tcttgcgatt tacgatacta tgcagtacat    360
tcgatctcca ataagcacga tttgtttagg ccaagctgcg tccatggctt ctctgctctt    420
ggcagcaggt gccaagggac agagacgggc acttccaaac gcgagcgtca tgattcatca    480
accttcagga ggatatagtg gacaagctaa ggatatgact atccacacga agcagattgt    540
tcgtgtttgg gatgctttga accagctgta cgtgaaacac acggggcaat ctattgatgt    600
gattgagaaa aacatggata gggatcattt catgactcct gaggaggcta aagcgtttgg    660
tataatagac gaagtgattg atgagagacc attggagctg gtgaaggatg ctgttggagg    720
tgaaagcaaa gataaaagtt gagagaaact ggtaatcaaa gaa                      763
```

```
<210> SEQ ID NO 13
<211> LENGTH: 291
<212> TYPE: DNA
<213> ORGANISM: Brassica napus

<400> SEQUENCE: 13
taaggttctt catatatttt aacgatttaa attgttgatt ggtacttatt garatgtttg     60
cacaggacct ggttgctcag cgatcgccac tggtgctgcg caagaactag gaccgtttct    120
ggtccatacc aaaggtggca acctcacctt caatgaattc tcttggaaca aaggtacaac    180
gaacattacc ataatgaaat gaccatttga agataatgaa tacatttatg tatacatttt    240
aataaatcaa tgtttgtgca gaggccaata tcttgttctt ggaagcaccg g             291
```

```
<210> SEQ ID NO 14
<211> LENGTH: 291
<212> TYPE: DNA
<213> ORGANISM: Brassica napus

<400> SEQUENCE: 14
taaggttctt catatatttt aacgatttaa attgttgatt ggtacttatt gagatgtttg     60
cacaggacct ggttgctcag cgatcgccac tggtgctgcg caagaactag gmccgtttct    120
ggtccatacc aaaggtggca acctcacctt caatgaattc tcttggaaca aaggtacaac    180
gaacattacc ataatgaaat gaccatttga agataatgaa tacatttatg tatacatttt    240
aataaatcaa tgtttgtgca gaggccaata tcttgttctt ggaagcaccg g             291
```

```
<210> SEQ ID NO 15
<211> LENGTH: 291
<212> TYPE: DNA
<213> ORGANISM: Brassica napus

<400> SEQUENCE: 15
taaggttctt catatatttt aacgatttaa attgttgatt ggtacttatt gagatgtttg     60
cacaggacct ggttgctcag cgatcgccac tggtgctgcg caagaactag gaccgtttct    120
ggtccatacc aaaggtggca acctcacctt caatgaattc tcttggaaca aaggtacaac    180
gaacattacc ataatgaaat kaccatttga agataatgaa tacatttatg tatacatttt    240
aataaatcaa tgtttgtgca gaggccaata tcttgttctt ggaagcaccg g             291
```

```
<210> SEQ ID NO 16
<211> LENGTH: 1645
<212> TYPE: DNA
<213> ORGANISM: Brassica napus
<220> FEATURE:
<221> NAME/KEY: misc_feature
<222> LOCATION: (12)..(13)
<223> OTHER INFORMATION: n is a, t, c, or g
```

-continued

```
<220> FEATURE:
<221> NAME/KEY: misc_feature
<222> LOCATION: (15)..(15)
<223> OTHER INFORMATION: n is a, t, c, or g
<220> FEATURE:
<221> NAME/KEY: misc_feature
<222> LOCATION: (18)..(18)
<223> OTHER INFORMATION: n is a, t, c, or g
<220> FEATURE:
<221> NAME/KEY: misc_feature
<222> LOCATION: (664)..(664)
<223> OTHER INFORMATION: n is a, t, c, or g
<220> FEATURE:
<221> NAME/KEY: misc_feature
<222> LOCATION: (757)..(757)
<223> OTHER INFORMATION: n is a, t, c, or g
<220> FEATURE:
<221> NAME/KEY: misc_feature
<222> LOCATION: (777)..(777)
<223> OTHER INFORMATION: n is a, t, c, or g
<220> FEATURE:
<221> NAME/KEY: misc_feature
<222> LOCATION: (794)..(794)
<223> OTHER INFORMATION: n is a, t, c, or g
<220> FEATURE:
<221> NAME/KEY: misc_feature
<222> LOCATION: (806)..(806)
<223> OTHER INFORMATION: n is a, t, c, or g
<220> FEATURE:
<221> NAME/KEY: misc_feature
<222> LOCATION: (816)..(816)
<223> OTHER INFORMATION: n is a, t, c, or g
<220> FEATURE:
<221> NAME/KEY: misc_feature
<222> LOCATION: (823)..(823)
<223> OTHER INFORMATION: n is a, t, c, or g
<220> FEATURE:
<221> NAME/KEY: misc_feature
<222> LOCATION: (840)..(841)
<223> OTHER INFORMATION: n is a, t, c, or g
<220> FEATURE:
<221> NAME/KEY: misc_feature
<222> LOCATION: (858)..(858)
<223> OTHER INFORMATION: n is a, t, c, or g
<220> FEATURE:
<221> NAME/KEY: misc_feature
<222> LOCATION: (870)..(870)
<223> OTHER INFORMATION: n is a, t, c, or g
<220> FEATURE:
<221> NAME/KEY: misc_feature
<222> LOCATION: (886)..(886)
<223> OTHER INFORMATION: n is a, t, c, or g
<220> FEATURE:
<221> NAME/KEY: misc_feature
<222> LOCATION: (899)..(899)
<223> OTHER INFORMATION: n is a, t, c, or g
<220> FEATURE:
<221> NAME/KEY: misc_feature
<222> LOCATION: (1012)..(1012)
<223> OTHER INFORMATION: n is a, t, c, or g
<220> FEATURE:
<221> NAME/KEY: misc_feature
<222> LOCATION: (1059)..(1059)
<223> OTHER INFORMATION: n is a, t, c, or g
<220> FEATURE:
<221> NAME/KEY: misc_feature
<222> LOCATION: (1082)..(1082)
<223> OTHER INFORMATION: n is a, t, c, or g
<220> FEATURE:
<221> NAME/KEY: misc_feature
<222> LOCATION: (1164)..(1164)
<223> OTHER INFORMATION: n is a, t, c, or g
<220> FEATURE:
<221> NAME/KEY: misc_feature
<222> LOCATION: (1363)..(1363)
<223> OTHER INFORMATION: n is a, t, c, or g
<220> FEATURE:
<221> NAME/KEY: misc_feature
<222> LOCATION: (1375)..(1375)
```

<223> OTHER INFORMATION: n is a, t, c, or g
<220> FEATURE:
<221> NAME/KEY: misc_feature
<222> LOCATION: (1526)..(1526)
<223> OTHER INFORMATION: n is a, t, c, or g
<220> FEATURE:
<221> NAME/KEY: misc_feature
<222> LOCATION: (1561)..(1561)
<223> OTHER INFORMATION: n is a, t, c, or g
<220> FEATURE:
<221> NAME/KEY: misc_feature
<222> LOCATION: (1570)..(1570)
<223> OTHER INFORMATION: n is a, t, c, or g
<220> FEATURE:
<221> NAME/KEY: misc_feature
<222> LOCATION: (1589)..(1589)
<223> OTHER INFORMATION: n is a, t, c, or g
<220> FEATURE:
<221> NAME/KEY: misc_feature
<222> LOCATION: (1610)..(1610)
<223> OTHER INFORMATION: n is a, t, c, or g
<220> FEATURE:
<221> NAME/KEY: misc_feature
<222> LOCATION: (1622)..(1622)
<223> OTHER INFORMATION: n is a, t, c, or g

<400> SEQUENCE: 16

```
ccacgcgtcc gnngnaangt attggcgatg aagaagaacg cactatggct actcctcgtt    60
ctcatgttgc cggcgatagc ctgcagtagg aaaccggaga agaaggtaac ggtctcgtcg   120
ggaaggaarg aggaagacct tgtgactggt ttgcccggtc aaccaccggt taacttccga   180
cattacgccg gttatgtcga tctagggcct cgacagaagc aaaagtcact tttctattgg   240
ttcttcgaag cccaacacaa ctcttctggt cgtcctctcg tcctttggct caacggagga   300
ccgggttgct catcggtagc ttatggagct gcacaagaac taggcccttt ccttgttcgc   360
accaacggtg gcaaccttac cttcaatgac ttctcttgga acaaagaggc caatatgttg   420
ttcttggaag cacctgtagg ggttggattc tcgtatacca ataactcagt ggatcttgga   480
aagcttgggg atcaagtaac tgcagaggac tcacttgatt tcttgatcaa ctggttcacg   540
aaatttcccg agttccggtc cagtgatttt tacctcaccg agagagtta cgccggtcac   600
tatgttcctc agcttgcaga ggtcatttac gacaggaaca agaaggttca aggagactct   660
cgcnatcaat ctcaagggtt tcatgattgg taacgcggcg atcaacgagg aaacagacat   720
ggcaggacta atagactacg catggagcca cgctatnagt atctgacgag ctccatnagt   780
aaccttcaca gcancgtgcg gtcttngatg aagagncaaa cgnagcaaca cgaccatacn   840
naatgctacg aaaacatnca aagctttcan tggaagctta caacgnatat cgacatatna   900
cagcatctat actcccgttt gcctctcctc tgtttcgtca tcttcttctt ctcaaagaag   960
acctaaactc gtcgtgtctc ctagtctctt tacttatcac gacatgtggg antaagtttc  1020
ctgcttccgg gtacgatcca tgcacagaag cctataccng aaaactactt taaccggaaa  1080
gnatgtgcag gttgcgctcc atgcgaacgt tacaaacctt ccttatccat acactccttg  1140
cagcggggta ataaggagat gggngtgagg caccatccac cgtgcttccc atcatccaga  1200
agcttttgac ggctggcctc cgcatttgga tctatagtgg agatactgat gggagagtac  1260
cagtaacatc tacgcgttat agcataaaga agatgggatc taaggtggag ttaccgtgga  1320
ggtcgtggtt ccacgagagt caagtggctg gatgggttga ganccttacgc cggganggact  1380
aactttttgct acagttagag gagctggtca tcaggttccg gtgtttgctc cggcacagtc  1440
tctcaccttg ttctctcact tcctttcttc caccccattg ccttcaaaac gcttctgatc  1500
attatcgcca attcatggca agttgnttat tgtcttgaaa ccgtcttgtg gtatttaacc  1560
```

```
ntacccaatn tgatacaatg agtttcaant taatcaaata aataaaaaan cccttttcaat    1620 gnctaaaaaa aaaaaaaaaa aaaaa                                          1645

<210> SEQ ID NO 17
<211> LENGTH: 1251
<212> TYPE: DNA
<213> ORGANISM: Brassica napus

<400> SEQUENCE: 17
aagtattggc gatgaagaag aacgcactat ggctactcct cgttctcatg ttgccggcga      60
tagcctgcag taggaaaccg gagaagaagg taacggtctc gtcgggaagg aaggaggaag    120
accttgtgac tggtttgccc ggtcaaccac cggttaactt ccgacattac gccggttatg    180
tcgatctagg gcctcgacag aagcaaaagt cacttttcta ttggttcttc gaagcccaac    240
acaactcttc tggtcgtcct ctcgtccttt ggctcaacgg aggaccgggt tgctcatcgg    300
tagcttatgg agctgcacaa gaactaggcc ctttccttgt tcgcaccaac ggtggcaacc    360
ttaccttcaa tgacttctct tggaacaaag aggccaatat gttgttcttg gaagcacctg    420
taggggttgg attctcgtat accaataact cagtggatct tggaaagctt ggggatcamg    480
taactgcaga ggactcactt gatttcttga tcaactggtt cacgaaattt cccgagttcc    540
ggtccagtga tttttacctc accggagaga gttacgccgg tcactatgtt cctcagcttg    600
cagaggtcat ttacgacagg aacaagaagg ttcaaggaga ctctcgcatc aatctcaagg    660
gtttcatgat tggtaacgcg gcgatcaacg aggaaacaga catggcagga ctaatagact    720
acgcatggag ccacgctata gtatctgacg agctccatag taaccttcac agcacgtgcg    780
gtcttgatga agagcaaacg agcaacacga ccatacaatg ctacgaaaac atcaaagctt    840
tcatggaagc ttacaacgat atcgacatat acagcatcta tactcccgtt tgcctctcct    900
ctgattcgtc atcttcttct tctcaaagaa gacctaaact cgtcgtgtct cctagtctct    960
ttacttaaca cgacatgtgg gataagtttc ctgcttccgg gtacgatcca tgcacagaag   1020
cctataccga aaactacttt aaccggaaag atgtgcaggt tgcgctccat gcgaacgtta   1080
caaaccttcc ttatccatac actccttgca gcggggtaat aaggagatgg ggtgaggcac   1140
catccaccgt gcttcccatc atccagaagc ttttgacggc tggcctccgc atttggatct   1200
atagtggaga tactgatggg agagtaccag taacatctac gcgttatagc a            1251

<210> SEQ ID NO 18
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 18
gaaggtgacc aagttcatgc tcaagaaccg attggatcat gcat                       44

<210> SEQ ID NO 19
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 19
gaaggtcgga gtcaacggat tcaagaaccg attggatcat gcac                       44
```

```
<210> SEQ ID NO 20
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 20
ggaggagagg aagagagacg atatt                                           25

<210> SEQ ID NO 21
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 21
gaaggtgacc aagttcatgc tgttcggcaa gaacgttttc cgaata                    46

<210> SEQ ID NO 22
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 22
gaaggtcgga gtcaacggat cggcaagaa cgttttccga atg                        43

<210> SEQ ID NO 23
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 23
ttgcagcaga tgggtgtctc tctt                                            24

<210> SEQ ID NO 24
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 24
gaaggtgacc aagttcatgc tattcgagag gtctggaaca acaact                    46

<210> SEQ ID NO 25
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 25
gaaggtcgga gtcaacggat tcgagaggtc tggaacaaca acc                       43

<210> SEQ ID NO 26
<211> LENGTH: 22
<212> TYPE: DNA
<213> ORGANISM: Artificial Sequence
<220> FEATURE:
<223> OTHER INFORMATION: synthetic oligonucleotide
```

-continued

```
<400> SEQUENCE: 26
gatctcgcgg atcagcgcga at                                             22

<210> SEQ ID NO 27
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 27
gaaggtgacc aagttcatgc tacactcagc cgatgagcaa gag                      43

<210> SEQ ID NO 28
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 28
gaaggtcgga gtcaacggat tacactcagc cgatgagcaa gac                      43

<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 29
gtcctcctct tcctcatacc acaa                                           24
```